(12) United States Patent
Takahashi et al.

(10) Patent No.: US 8,741,513 B2
(45) Date of Patent: Jun. 3, 2014

(54) METHOD FOR PREPARING ALIZARIN DERIVATIVE COMPOUND, NOVEL ALIZARIN DERIVATIVE COMPOUND, SURFACE MODIFICATION METHOD, PHOTOELECTRIC CONVERSION FILM, PHOTOELECTRIC CONVERSION ELEMENT, AND ELECTROPHOTOGRAPHIC PHOTORECEPTOR

(75) Inventors: Keita Takahashi, Kanagawa (JP); Kazumi Nii, Kanagawa (JP); Kazunari Yagi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/513,197

(22) PCT Filed: Dec. 3, 2010

(86) PCT No.: PCT/JP2010/072181
§ 371 (c)(1),
(2), (4) Date: Jun. 1, 2012

(87) PCT Pub. No.: WO2011/071130
PCT Pub. Date: Jun. 16, 2011

(65) Prior Publication Data
US 2012/0244462 A1      Sep. 27, 2012

(30) Foreign Application Priority Data

Dec. 7, 2009  (JP) ................................ 2009-277962
Mar. 19, 2010 (JP) ................................ 2010-064060

(51) Int. Cl.
*G03G 15/04*    (2006.01)
*G03G 5/04*     (2006.01)
*C07C 50/34*    (2006.01)
*H01L 31/04*    (2014.01)
*H01L 51/42*    (2006.01)

(52) U.S. Cl.
USPC ............... 430/60; 430/62; 552/209; 552/219; 552/224; 552/260; 552/261

(58) Field of Classification Search
USPC ............. 430/60, 62; 552/209, 219, 224, 260, 552/261
See application file for complete search history.

(56) References Cited

U.S. PATENT DOCUMENTS

2006/0014090 A1*  1/2006  Shiino et al. ................. 430/59.1

OTHER PUBLICATIONS

Synthesis, 1991,438.
Angew. Chem. Int. Ed., 2008,47, 10128.
Inorg. Chem.,2001,40, 4361.
J. Chem. Soc., 1962, 83.

Ber. Deu. Chem. Gese. B , 1921, 54B, 3035.
Bioorg. Med. Chem. Lett., 2006, 16, 4512.
Ind. J. Chem., Sec. B (Org. Chem. Med. Chem.), 2004, 44G, 1970.
Aus. J. Chem., 1976, 29, 2231.
Phytochemistry, 1979, 18, 906.
Acta Mycologica, 1979, 15, 183.
Current Science, 1985, 54, 998.

(Continued)

*Primary Examiner* — Thorl Chea
(74) *Attorney, Agent, or Firm* — SOLARIS Intellectual Property Group, PLLC

(57) ABSTRACT

The present invention provides a novel alizarin derivative compound and a simplified and low cost method for preparing an alizarin derivative compound including: obtaining a compound represented by Formula (2) using a compound represented by Formula (3); and obtaining an alizarin derivative compound represented by Formula (1) using the compound represented by Formula (2); in Formulae (1) to (3), $R^1$ represents a hydrogen atom or a substituent; n represents an integer of 1 to 3, L represents a specific alkyl group; Q represents an atomic group needed to form an aromatic ring or a heteroaromatic ring with adjacent carbon atoms; and P represents an atomic group which includes an atom(s) selected from a hydrogen atom, a carbon atom, an oxygen atom, a sulfur atom, a silicon atom and a boron atom, and which is needed to form a ring structure group with adjacent two oxygen atoms and two carbon atoms;

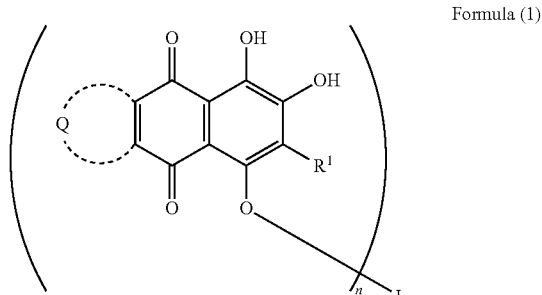

Formula (1)

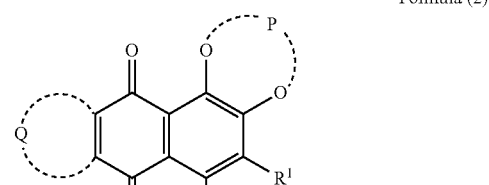

Formula (2)

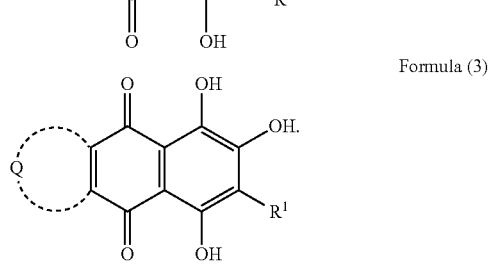

Formula (3)

11 Claims, 1 Drawing Sheet

(56) References Cited

OTHER PUBLICATIONS

Chinese Journal of Synthetic Chemistry vol. 16, 2008, No. 133-135. Partial English language translation of the following: Office action dated Jan. 21, 2014 from the Chinese Patent Office in a Chinese patent application corresponding to the instant patent application. This office action translation is submitted now in order to supplement the understanding of non-patent literature document Chinese Journal of Synthetic Chemistry vol. 16, 2008, No. 133-135 which are cited in the office action and are being disclosed in the instant Information Disclosure Statement.

\* cited by examiner

US 8,741,513 B2

METHOD FOR PREPARING ALIZARIN DERIVATIVE COMPOUND, NOVEL ALIZARIN DERIVATIVE COMPOUND, SURFACE MODIFICATION METHOD, PHOTOELECTRIC CONVERSION FILM, PHOTOELECTRIC CONVERSION ELEMENT, AND ELECTROPHOTOGRAPHIC PHOTORECEPTOR

BACKGROUND OF THE INVENTION

1. Technical Field

The present invention relates to a method for preparing an alizarin derivative compound, a novel alizarin derivative compound, a surface modification method and surface-modified particles using the alizarin derivative compound, and a photoelectric conversion film, a photoelectric conversion element, and an electrophotographic photoreceptor including the alizarin derivative compound as a component.

2. Background Art

An alizarin derivative compound is a compound which can be applied in a wide range of various fields, such as compounds, complexes, and Lake pigments that are used in organic electronics fields (for example, dye-sensitized solar cells, organic thin film solar cells, organic imaging elements, organic semiconductors, organic EL elements, electrophotographic photoreceptors, and the like), color material fields (for example, inks for inkjet, color copies in a sublimation transfer mode, ink dyes, color filters, silver halide photosensitive materials, printing, optical recording media, colorants for food, and the like), physiologically active materials (for example, anticancer agents, hair growth promoters, and the like), electrolyte solutions, and the like.

As a compound modified at the 4-position, starting from purpurin (a compound represented by the following structural formula), only a few examples have been hitherto reported.

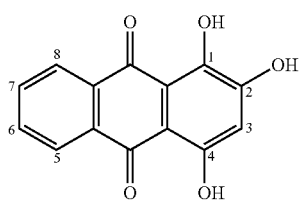 [SMILES: O=C1c2ccccc2C(=O)c2c(O)c(O)cc(O)c21]

As a method for synthesizing a product obtained by modification of the 4-position of purpurin, for example, a synthesis method shown below is described in Synthesis, 1991, p. 438. In addition, the strength levels of the binding capabilities of the product obtained by modification of the 4-position of purpurin with various metal oxides are discussed using compounds obtained by methylation of the 4-position of purpurin in Angew. Chem. Int. Ed., 2008, vol. 47, p. 10128.

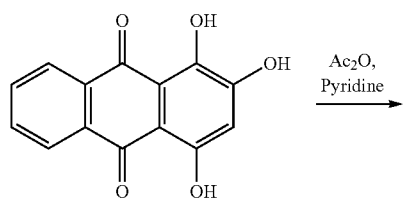

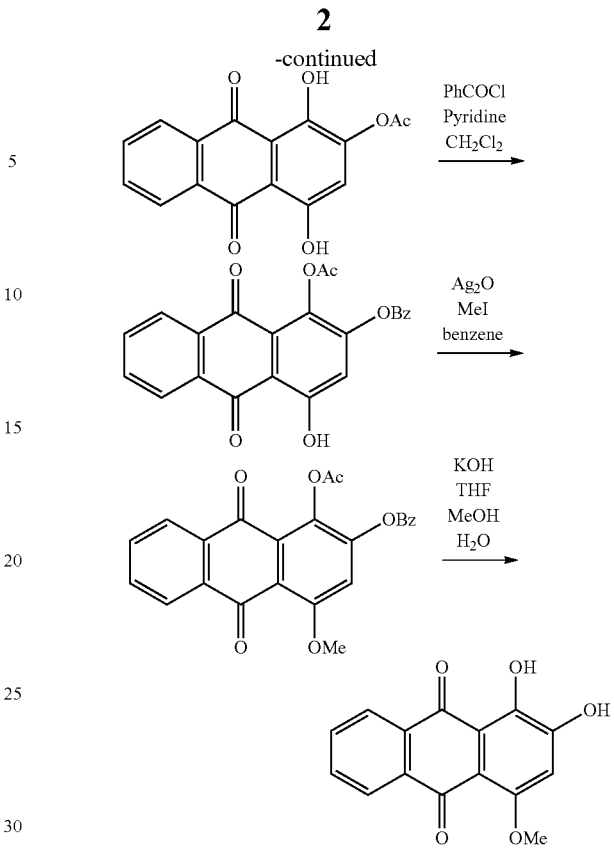

Furthermore, a synthesis method for obtaining a product obtained by modification of the 4-position of purpurin in a short step by protecting a catechol part of purpurin with Ru metal and then introducing an alkyl group thereinto is suggested in Inorg. Chem., 2001, vol. 40, p. 4361.

In addition, there is a report of a modification method for modifying the 4-position of alizarin in a short step by adding a nitro group or bromine to alizarin, then converting the alizarin into an oxidized product, and adding an alcohol thereto (see, for example, J. Chem. Soc., 1962, p. 83, or Ber. Deu. Chem. Gese. B, 1921, vol. 54 B, p. 3035).

Further, as for a novel alizarin derivative compound, isolation by extraction from a natural product/determination of structures/physiological activity (anti-fungus agents), and the like have been found (see Bioorg. Med. Chem. Lett., 2006, vol. 16, p. 4512, Ind. J. Chem., Sec. B (Org. Chem. Med. Chem.), 2004, vol. 44 G, p. 1970, Aus. J. Chem., 1976, vol. 29, p. 2231, Phytochemistry, 1979, vol. 18, p. 906, Acta Mycologica, 1979, vol. 15, p. 183, or Current Science, 1985, vol. 54, p. 998).

There is a demand for a method for synthesizing an alizarin derivative compound formed by using purpurin or the like as a starting raw material and modifying the 4-position of the anthraquinone skeleton in a simple manner and at low cost, but the synthesis methods described in the Non-Patent Documents indicated above suffer from the following problems.

That is, the synthesis method described in Synthesis, 1991, p. 438 not only requires four steps until a desired product is synthesized, but also, it is necessary to use expensive silver oxide in an excessive amount in a third step, resulting in low suitability for production.

Further, according to investigations by the present inventors, it has been confirmed that an alizarin derivative compound (Me-modified product at the 4-position of purpurin) as obtained in Synthesis, 1991, p. 438 returns to purpurin due to deprotection with a MeO group when heated with a Lewis acid, and thus, the stability is threatened in the case of applying the compound in various applications.

In the synthesis method described in Inorg. Chem., 2001, vol. 40, p. 4361, suitability for production is low in view of the use of an expensive metal. Further, in this document, there is no investigation regarding deprotection of a Ru complex part. In addition, in this document, there is only an investigation regarding a methyl-substituted product as a product obtained by modification of the 4-position of purpurin.

In the synthesis method for adding an alcohol through oxidation from nitroalizarin as described in J. Chem. Soc., 1962, p. 83, the 4-position of alizarin can be modified in a short step, but the resulting modified product has low stability. Further, as for a synthesis method, there is risk involved due to the coexistence of an oxidant and an alcohol, and thus its suitability for production is low.

In the method for addition of an alcohol through oxidation involving addition of bromine from alizarin as described in Ber. Deu. Chem. Gese. B, 1921, vol. 54B, p. 3035, the 4-position of alizarin can be modified in a short step, but a desired compound is not necessarily obtained by adding bromine, and further, it easily becomes a complex mixture. According to practical investigations by the present inventors, additional testing has been impossible.

Furthermore, in the methods described in Bioorg. Med. Chem. Lett., 2006, vol. 16, p. 4512, Ind. J. Chem., Sec. B (Org. Chem. Med. Chem.), 2004, vol. 44G, p. 1970, Aus. J. Chem., 1976, vol. 29, p. 2231, Phytochemistry, 1979, vol. 18, p. 906, Acta Mycologica, 1979, vol. 15, p. 183, and Current Science, 1985, vol. 54, p. 998, suitability for production is also low.

Moreover, in the case of using purpurin as a raw material, purpurin which is available as a commercial product (for example, products manufactured by Tokyo Chemical Industry Co., Ltd. and Kanto Chemical Co., Ltd. are available) contains quinizarin (a compound having the following structure) as an impurity in an amount of about 15%. According to the investigations by the present inventors, it has been proven that if such purpurin is used as a raw material in the above-described synthesis method, a large degree of loss is involved in the separation of quinizarin, thereby resulting in even lower suitability for production.

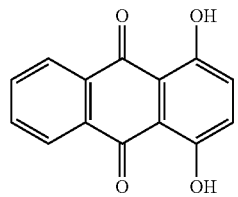 [SMILES: O=C1c2ccccc2C(=O)c2c(O)ccc(O)c21]

On the other hand, from the viewpoint that an alizarin derivative compound such as a product obtained by modification of the 4-position of purpurin, or the like can modify the surface of an inorganic compound solid material such as a metal oxide or the like using the coordination bond with the surface, there is a demand for a compound which has various substituents introduced to the 4-position of purpurin and stably forms a complex with the metal oxide in order to adjust the physical properties of the surface of the inorganic compound solid material while not weakening the coordination capability, and a method for preparing the same, which have hitherto not been provided.

SUMMARY OF THE INVENTION

According to an aspect of the invention, a novel alizarin derivative compound and a simplified and low cost method for preparing an alizarin derivative compound including: (A) obtaining a compound represented by the following Formula (2) using a compound represented by the following Formula (3); and (B) obtaining an alizarin derivative compound represented by the following Formula (1) using the compound represented by Formula (2) obtained by the step (A); in Formulae (1) to (3), $R^1$ represents a hydrogen atom or a substituent; n represents an integer of 1 to 3, L represents a specific alkyl group; Q represents an atomic group needed to form an aromatic ring or a heteroaromatic ring with adjacent carbon atoms; and P represents an atomic group which includes an atom(s) selected from a hydrogen atom, a carbon atom, an oxygen atom, a sulfur atom, a silicon atom and a boron atom, and which is needed to form a ring structure group with adjacent two oxygen atoms and two carbon atoms, are provided.

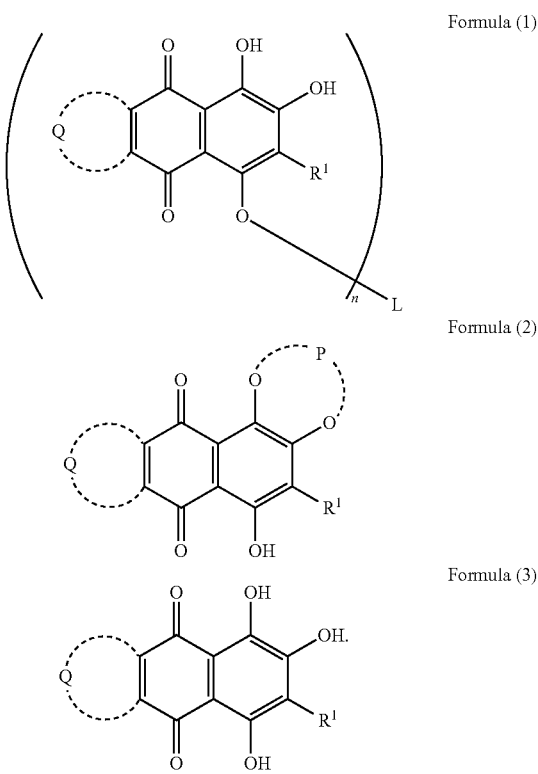

Technical Problem

The present invention has been made in view of the above circumstances and it is an object thereof to provide a preparation method for obtaining an alizarin derivative compound in a simple manner and at low cost by using purpurin as a starting material and modifying the 4-position thereof, and a novel alizarin derivative compound to which the preparation method can be applied.

It is another object of the present invention to provide a surface modification method for an inorganic compound solid material using the novel alizarin derivative compound.

It is a further another object of the present invention to provide a photoelectric conversion film, a photoelectric conversion element, and an electrophotographic photoreceptor, having the novel alizarin derivative compound as a component.

Solution to Problem

As a result of the earnest investigation made by the present inventors in view of the above problems, it has been found that the objects of the invention can be achieved by the following means. Exemplary embodiments of the present invention include the followings.

<1> A method for preparing an alizarin derivative compound including: (A) obtaining a compound represented by the following Formula (2) using a compound represented by the following Formula (3); and (B) obtaining an alizarin derivative compound represented by the following Formula (1) using the compound represented by Formula (2) obtained by the step (A);

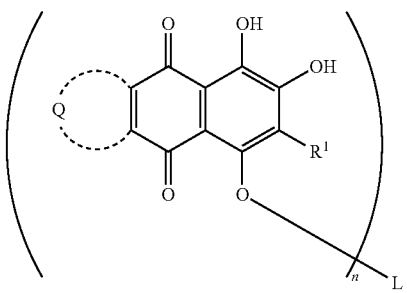

Formula (1)

wherein, in Formula (1), $R^1$ represents a hydrogen atom or a substituent; n represents an integer of 1 to 3, when n is 1, L represents —$C(R^{a1})(R^{a2})(R^{a3})$; $R^{a1}$, $R^{a2}$, and $R^{a3}$ each independently represent a hydrogen atom, a substituted or unsubstituted alkyl group having 1 to 30 carbon atoms, or a substituted or unsubstituted aryl group having 6 to 30 carbon atoms; at least one of $R^{a1}$, $R^{a2}$, and $R^{a3}$ represents a substituted or unsubstituted alkyl group having 1 to 30 carbon atoms, or a substituted or unsubstituted aryl group having 6 to 30 carbon atoms; when n is 2, L represents a substituted or unsubstituted divalent linkage group having 2 to 20 carbon atoms; when n is 3, L represents a substituted or unsubstituted trivalent linkage group having 2 to 30 carbon atoms; and Q represents an atomic group which is needed to form an aromatic ring or a heteroaromatic ring with adjacent carbon atoms;

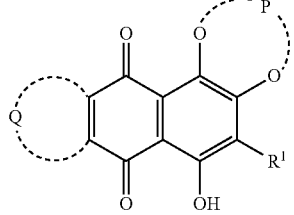

Formula (2)

wherein, in Formula (2), P represents an atomic group which includes an atom(s) selected from a hydrogen atom, a carbon atom, an oxygen atom, a sulfur atom, a silicon atom and a boron atom, and which is needed to form a ring structure group with two adjacent oxygen atoms and two carbon atoms; and each of $R^1$ and Q has the same definition as $R^1$ and Q in Formula (1) respectively;

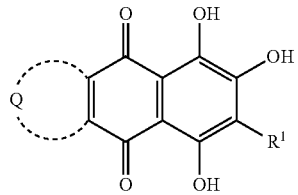

Formula (3)

and wherein, in Formula (3), each of $R^1$ and Q has the same definition as $R^1$ and Q in Formula (1) respectively.

<2> The method for preparing an alizarin derivative compound according to the item <1>, wherein the step (B) includes: (B1) obtaining a compound represented by the following Formula (4) using the compound represented by Formula (2); and (B2) obtaining the alizarin derivative compound represented by Formula (1) using the compound represented by Formula (4) obtained by the step (B1);

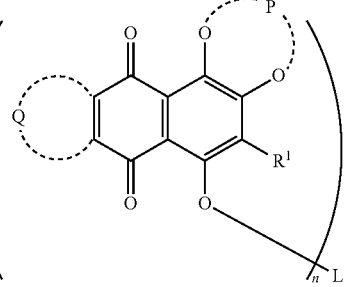

Formula (4)

wherein, in Formula (4), P has the same definition as P in Formula (2); and each of $R^1$, L, n and Q has the same definition as $R^1$, L, n and Q in Formula (1) respectively.

<3> An alizarin derivative compound represented by the following Formula (5);

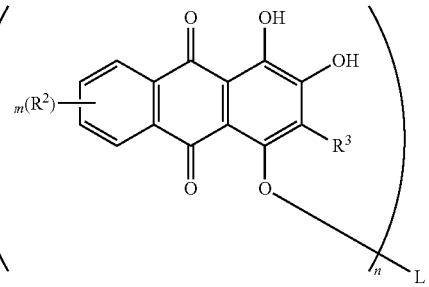

Formula (5)

wherein, in Formula (5), $R^2$ represents a hydrogen atom, a substituted or unsubstituted alkyl group having 1 to 30 carbon atoms, a substituted or unsubstituted aryl group having 6 to 30 carbon atoms, or a substituted or unsubstituted alkoxy group having 1 to 30 carbon atoms; m represents an integer of 0 to 4; $R^3$ represents a hydrogen atom, a substituted or unsubstituted alkyl group having 1 to 30 carbon atoms, a substituted or unsubstiunsubstituted aryl group having 6 to 30 carbon atoms, or a substituted or unsubstituted alkoxy group having 1 to 30 carbon atoms; n represents an integer of 1 to 3; when n is 1, L represents —C($R^{a1}$)($R^{a2}$)($R^{a3}$); $R^{a1}$, $R^{a2}$, and $R^{a3}$ each independently represent a hydrogen atom, a substituted or unsubstituted alkyl group having 1 to 30 carbon atoms, or a substituted or unsubstituted aryl group having 6 to 30 carbon atoms; at least one of $R^{a1}$, $R^{a2}$, and $R^{a3}$ represents a substituted or unsubstituted alkyl group having 1 to 30 carbon atoms, or a substituted or unsubstituted aryl group having 6 to 30 carbon atoms; when n is 2, L represents a substituted or unsubstituted divalent linkage group having 2 to 20 carbon atoms; and when n is 3, L represents a substituted or unsubstituted trivalent linkage group having 2 to 30 carbon atoms.

<4> The alizarin derivative compound according to the item <3>, wherein the alizarin derivative compound represented by Formula (5) is an alizarin derivative compound represented by the following Formula (6);

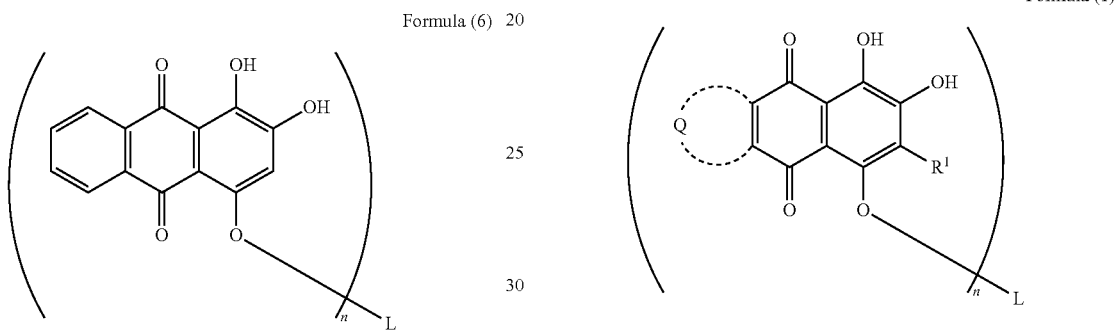

Formula (6)

wherein, in Formula (6), each of n and L has the same definition as n and L in Formula (5) respectively.

<5> A surface modification method for an inorganic compound solid material, the method including bonding the alizarin derivative compound according to the item <3> or the item <4> to a surface of an inorganic compound solid material through an oxygen atom obtained by removal of a hydrogen atom from at least one hydroxyl group contained in the alizarin derivative compound.

<6> The surface modification method for an inorganic compound solid material according to the item <5>, wherein the inorganic compound solid material is a metal oxide.

<7> The surface modification method for an inorganic compound solid material according to the item <5>, wherein the inorganic compound solid material is a fine particle of a metal oxide.

<8> The surface modification method for an inorganic compound solid material according to the item <6> or the item <7>, wherein the metal oxide is selected from the group consisting of $TiO_2$, $Al_2O_3$, $SiO_2$, $ZrO_2$ and ZnO.

<9> A photoelectric conversion film including the alizarin derivative compound according to the item <3> or the item <4>.

<10> A photoelectric conversion element including the alizarin derivative compound according to the item <3> or the item <4>.

<11> An electrophotographic photoreceptor including a conductive base, an undercoat layer on the conductive base and a photosensitive layer, wherein the undercoat layer includes the alizarin derivative compound according to the item <3> or the item <4>.

BRIEF DESCRIPTION OF DRAWINGS

Exemplary embodiments of the invention will be described in detail based on the following figures, wherein.

DESCRIPTION OF EMBODIMENTS

Method for Preparing Alizarin Derivative Compound

Figure 1A:
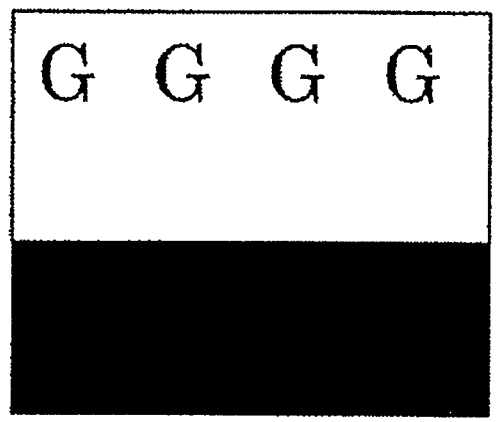
FIGS. 1A to 1C are each a drawing showing the image pattern and the criteria for evaluating ghost generation in the image.

The method for preparing an alizarin derivative compound of the present invention (which is hereinafter also simply referred to as "the preparation method of the present invention") is characterized by including a step (A) of obtaining a compound represented by the following Formula (2) using a compound represented by the following Formula (3), and a step (B) of obtaining an alizarin derivative compound represented by the following Formula (1) using the compound represented by Formula (2) obtained by the step (A).

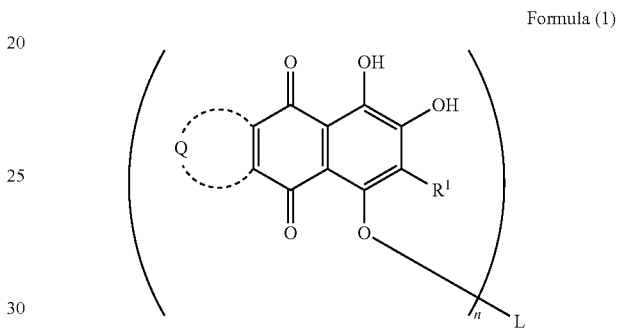

Formula (1)

In Formula (1), $R^1$ represents a hydrogen atom or a substituent. n represents an integer of 1 to 3. When n is 1, L represents —C($R^{a1}$)($R^{a2}$)($R^{a3}$). $R^{a1}$, $R^{a2}$, and $R^{a3}$ each independently represent a hydrogen atom, a substituted or unsubstituted alkyl group having 1 to 30 carbon atoms, or a substituted or unsubstituted aryl group having 6 to 30 carbon atoms. Here, at least one of $R^{a1}$, $R^{a2}$, and $R^{a3}$ represents a substituted or unsubstituted alkyl group having 1 to 30 carbon atoms, or a substituted or unsubstituted aryl group having 6 to 30 carbon atoms. When n is 2, L represents a substituted or unsubstituted divalent linkage group having 2 to 20 carbon atoms. When n is 3, L represents a substituted or unsubstituted trivalent linkage group having 2 to 30 carbon atoms. Q represents an atomic group which is needed to form an aromatic ring or a heteroaromatic ring with adjacent carbon atoms.

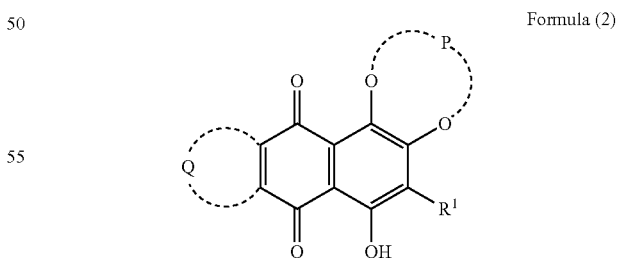

Formula (2)

In Formula (2), P represents an atomic group which includes an atom(s) selected from a hydrogen atom, a carbon atom, an oxygen atom, a sulfur atom, a silicon atom and a boron atom, and which is needed to form a ring structure with two adjacent oxygen atoms and two carbon atoms; and each of $R^1$ and Q has the same definition as $R^1$ and Q in Formula (1) respectively.

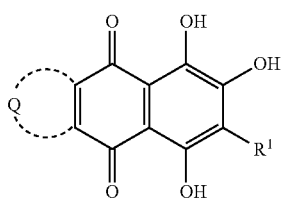

Formula (3)

In Formula (3), each of $R^1$ and Q has the same definition as $R^1$ and Q in Formula (1) respectively.

Hereinbelow, each of the steps in the preparation method of the present invention will be described.

Furthermore, the details on each of the compounds such as the alizarin derivative compound represented by Formula (1) above obtained by the preparation method of the present invention, the compound represented by Formula (3) above to be used as a starting raw material, the compound represented by Formula (2) above which is produced as an intermediate, and the like will be described specifically, following the description of each step in the preparation method of the present invention.

<Step (A)>

The step (A) is a protection step in which a catechol moiety included in the compound is protected with a protecting group, thereby obtaining the compound represented by Formula (2), using a compound represented by Formula (3) as a starting raw material. The protecting group is a moiety represented by a ring structure including "P" in Formula (2).

In the step (A), when it is attempted to obtain the compound represented by Formula (2) by protecting a cathecol moiety in the compound represented by Formula (3) with a protecting group, the compound can be obtained by reacting a compound selected from the compounds exemplified in the compound group A with the cathecol moiety, thereby forming a protecting group. Furthermore, the compound which can be used to form the protecting group is not limited to the compounds exemplified in the compound group A.

—Compound Group A—

Ketones (acetone, methyl ethyl ketone, cyclohexanone, benzophenone, and the like); acetals (acetone dimethyl acetal, methyl ethyl ketone dimethyl acetal, cyclohexanone dimethyl acetal, benzophenone dimethyl acetal, and the like); dihalomethanes (bromochloromethane, dibromomethane, dichlorodimethylmethane, dichlorodiphenylmethane, and the like); ortho esters (trimethyl orthoformate, triethyl orthoformate, trimethyl orthoacetate, triethyl orthoacetate, triethyl orthobutylate, and the like); carbonates (dimethyl carbonate, diphenyl carbonate, and the like); silanes (dichlorodimethylsilane, dichlorodiethylsilane, dichlorodiphenylsilane, dimethyldimethoxysilane, and the like); boron compounds (boric acid, borax, phenylboronic acid, an the like); and the like are exemplified. Among the above, ketones, acetals, dihalomethanes, ortho esters, and boron compounds are preferable, and dihalomethanes are most preferable.

Here, dihalomethanes, which are preferable examples of the compound that can be used to form a protecting group, can be derived from the corresponding ketones. For example, dihalodiphenylmethanes and dihalodimethylmethanes are derived from benzophenone and acetone, respectively.

The reaction with corresponding dihalomethanes from ketones can be carried out according to known examples described in the documents such as "J. Med. Chem., 2008, vol. 51, p. 2115", "Organic Preparations and Procedures International, 1992, vol. 24, p. 60", "J. Org. Chem., 1968, vol. 33, p. 4317", and the like.

The corresponding dihalomethanes can be synthesized by using chlorine sources such as chlorine, phosphorus pentachloride, phosphorus oxychloride, thionyl chloride, and the like for dichlorination of ketones, using bromine sources such as bromine, phosphorus pentabromide, phosphorus oxybromide, thionyl bromide, and the like for dibromination, and using iodine sources such as iodine and the like for diiodination.

Herein, activators such as N,N'-dimethylformamide (DMF), N,N'-dimethylacetamide (DMAc), pyridine, N,N-dimethyl-4-amino pyridine (DMAP), and the like can be used in combination therewith.

The amount of halogen sources (chlorine sources, bromine sources, and iodine sources) to be used is preferably in the range of from 1 mole to 100 moles, more preferably from 1.5 moles to 50 moles, and most preferably from 2.0 moles to 25 moles, with respect to moles of ketones.

In the case of using an activator, the amount of the activator is preferably in the range of from 0.01 mole to 100 moles, more preferably from 0.1 mole to 50 moles, and most preferably from 1 mole to 10 moles with respect to moles of ketones.

The reaction temperature in the synthesis of dihalomethanes is preferably in the range of from 0° C. to 150° C., more preferably in the range from 25° C. to 100° C., and further more preferably in the range from 40° C. to 90° C.

The mole amount of the compound used to form a protecting group is preferably in a range of from 0.1 moles to 100 moles, more preferably from 0.5 moles to 10 moles, and most preferably from 1 mole to 5 moles with respect to 1 mole of the compound represented by Formula (3).

The conditions which are needed to form "a ring structure formed with an atom group represented by P" which is a protecting group shown in Formula (2) may be any one of acidic conditions, basic conditions, and neutral conditions. Among them, acidic conditions or basic conditions are preferable, and basic conditions are most preferable.

The acid which is used in the case of carrying out the protection under acidic conditions may be any one of an inorganic acid and an organic acid. As the inorganic acid, mineral acids (for example, sulfuric acid, hydrochloric acid, hydrobromic acid, nitric acid, phosphoric acid, and the like) are preferred, and as the organic acid, organic carboxylic acids (for example, acetic acid, oxalic acid, formic acid, propionic acid, benzoic acid, and the like), and sulfonic acids (for example, methanesulfonic acid, ethanesulfonic acid, benzenesulfonic acid, p-toluenesulfonic acid, and the like) are preferably used, and sulfuric acid, hydrochloric acid, acetic acid, and p-toluenesulfonic acid are more preferable, and sulfuric acid and hydrochloric acid are most preferable. In addition, these acids may be used alone or as a mixture of two or more kinds thereof.

The amount of the acid used in the reaction is preferably 0.01 mole to 5.0 moles, and more preferably 0.1 mole to 1.0 mole, based on 1 mole of the phenolic hydroxyl group contained in the substrate used in the reaction.

The base used in the case of carrying out the protection under basic conditions may be any one of an inorganic base and an organic base. As the inorganic base, alkali metal carbonates (potassium carbonate, sodium carbonate, cesium carbonate, and the like), alkali metal hydroxides (sodium hydroxide, potassium hydroxide, and the like), alkali metal phosphates (trisodium phosphate, tripotassium phosphate, and the like), other metal alkoxides (for example, sodium alkoxide, lithium alkoxide, and the like, and alkoxide derivatives formed in an alcohol solvent), and alkyl metals (for example, methyl lithium, n-butyl lithium, and the like) are preferable, and as the organic base, alkyl amines (triethylamine and the like), organic strong bases (for example, 1,8-diazabicyclo[5,4,0]-7-undecene, 1,5-diazabicyclo[4,3,0]-5-nonene, and the like), and the like are preferable. More preferably, the base is an alkali metal carbonate, an alkali metal hydroxide, or an alkyl amine, and most preferably, an alkali metal carbonate or an alkali metal hydroxide. Further, these bases may be used alone or as a mixture of two or more kinds thereof.

The amount of the base used in the reaction is preferably 1.0 mole to 5.0 moles, and more preferably 1.0 mole to 3.0 moles, based on 1 mole of the phenolic hydroxyl group contained in the substrate used in the reaction. Further, in the case of using an inorganic base, as the form of the inorganic base used in the reaction, an inorganic base in the form of pellet, an inorganic base in the form of granule, or an inorganic base in the form of powder may be used as it is, but an inorganic base in the form of powder is preferably used as it is.

For the purpose of promoting the reaction in the protection step, phase transfer catalysts or crown ethers can also be used.

A phase transfer catalyst which is usable in the reaction of the exemplary embodiment of the invention is described below.

Examples of cationic part(s) of the phase transfer catalyst include tetraalkylammoniums such as tetraethylammonium, tetrabutylammonium, tetraoctylammonium, dodecyltrimethylammonium, tributylmethylammonium, and the like; aralkyltrialkylammoniums such as benzyltrimethylammonium, benzyltriethylammonium, benzyltributylammonium, benzyltriamylammonium, benzylethyldibutylammonium, phenethyltriethylammonium, phenethyltributylammonium, phenethylbutyldiethylammonium and the like; cyclic oniums such as, diethylpyrrolinium, dibutylpyrrolinium, dihexylpyrrolinium, methylbenzylpyrrolinium, diethylpyrrolidinium, dibutylpyrrolidinium, dihexylpyrrolidinium, ethylbenzylpyrrolidinium, diethylpiperidinium, dibutylpiperidinium, dihexylpiperidinium, methylbenzylpiperidinium, diethylindolinium, dibutylindolinium, dihexylindolinium, ethylbenzylindolinium, diethylmorpholinium, dibutylmorpholinium, dihexylmorpholinium, methylbenzylmorpholinium, diethylthiazinium, dibutylthiazinium, dihexylthiazinium, ethylbenzylthiazinium, butylpyridinium, hexylpyridinium, octylpyridinium, laurylpyridinium, benzylpyridinium, tetramethylpiperazinium, tetraethylpiperazinium, dimethyldibutylpiperazinium, dimethyldihexylpiperazinium, dimethyldibenzylpiperazinium, tetramethylimidazolidinium, tetraethylimidazolidinium, dimethyldibutylimidazolidinium, dimethyldihexylimidazolidinium, dimethyldibezylimidazolidinium, and the like; tetraarylammoniums such as tetraphenylammonium, and the like; tetraalkylphosphoniums such as tetraethylphosphonium, tetrabutylphosphonium, and the like; and tetraarylphosphoniums such as tetraphenylphosphonium, and the like. Among them, tetraalkylammoniums such as tetraethylammonium, tetrabutylammonium, tetraoctylammonium, dodecyltrimethylammonium, tributylmethylammonium, and the like; and tetraalkylphosphoniums such as tetraethylphosphonium, tetrabutylphosphonium, and the like are preferable. Further, oniums described in Japanese Patent Application Laid-Open (JP-A) Nos. 2004-226794, 2004-233854 and the like are exemplified.

Examples of the anion part of the phase transfer catalyst include halogen ions, $BF_4^-$, $AsF_6^-$, $PF_6^-$, $SbF_6^-$, $SiF_6^{2-}$, $ClO_4^-$, organic carboxylic acid ions such as hydroxide ions, nitric acid ions, sulfuric acid ions, hydrogensulfate ions, carbonic acid ions, hydrogen carbonate ions, formic acid ions, oxalic acid ions, acetic acid ions, propionic acid ions, succinic acid ions, cinnamic acid ions, trifluoroacetic acid ions, benzoic acid ions, and the like, alkane sulfonic acid ions which may be substituted, such as methane sulfonic acid ions, ethane sulfonic acid ions, butane sulfonic acid ions, chloromethane sulfonic acid ions, fluoromethane sulfonic acid ions, dichloromethane sulfonic acid ions, bromoethane sulfonic acid ions, and the like, perfluoroalkane sulfonic acid ions such as trifluoromethane sulfonic acid ions, pentafluoroethane sulfonic acid ions, heptafluoropropane sulfonic acid ions, and the like, benzene sulfonic acid ions which may be substituted, such as toluene sulfonic acid ions, p-chlorobenzene sulfonic acid ions, p-cyanobenzene sulfonic acid ions, p-acylaminobenzene sulfonic acid ions, and the like, naphthalene sulfonic acid ions, anthracene sulfonic acid ions, camphor sulfonic acid ions, alkane phosphonic acid ions which may be substituted, aryl phosphonic acid ions which may be substituted, camphor phosphonic acid ions, and the like, but are not limited thereto. Among these, as the anion part, hydroxide ions, hydrogensulfate ions, chlorine ions, bromine ions, and iodine ions are preferable; hydroxyl ions, chlorine ions, bromine ions, and iodine ions are more preferable; and bromine ions and iodine ions are particularly preferable.

Examples of crown ethers include, in addition to the crown ether, cryptand, calixarene, and polyether compounds such as polyalkylene glycol ether and the like.

As the crown ether, for example, a 12-crown 4-ether, a 15-crown 5-ether, an 18-crown 6-ether, a 24-crown 8-ether, and the like are preferable.

As the cryptand, for example, [1,1,1]cryptand, [2,1,1]cryptand, [2,2,1]cryptand, [2,2,2]cryptand, and the like are preferable.

As the calixarene, for example, calix[4]arene, calix[5]arene, calix[6]arene, and the like are preferable.

Polyether compounds other than cyclic ethers such as the crown ethers or cryptand compounds are usable as a polyether compound, but are not limited thereto. Among them, ethylene glycol dimethyl ether, ethylene glycol diethyl ether, ethylene glycol dibutyl ether, diethylene glycol dimethyl ether, diethylene glycol diethyl ether, diethylene glycol dibutyl ether, triethylene glycol dimethyl ether, triethylene glycol diethyl ether, triethylene glycol dibutyl ether, tetraethylene glycol dimethyl ether, tetraethylene glycol diethyl ether, tetraethylene glycol dibutyl ether and the like are preferable.

The amount of the phase transfer catalysts used or crown ethers which are used in the reaction is preferably 0.01 mol % to 200 mol %, more preferably 0.5 mol % to 100 mol %, and particularly preferably 1 mol % to 50 mol %, based on 1 mole of the phenolic hydroxyl group contained in the substrate used in the reaction.

These phase transfer catalysts or crown ethers may be used as a single body or as a solution, and may also be used after being fixed on a polymer.

The phase transfer catalysts or crown ethers may be used alone or as a mixture of two or more kinds thereof.

The step (A) can be carried out by, for example, the method described in "Protecting Groups in Organic Synthesis $3^{rd}$ Edition 1999 John Wiley & Sons, Inc.".

<Step (B)>

In the step (B), the alizarin derivative compound represented by Formula (1) above is obtained by subjecting the compound represented by Formula (2) obtained in the step (A) to alkylation of the 4-position and deprotection of a cathecol moiety.

The step (B) is specifically a step including a substep (B1) which is an alkylation step for obtaining a compound represented by the following Formula (4) using the compound represented by Formula (2) above and a substep (B2) which is a deprotection step for obtaining the alizarin derivative compound represented by Formula (1) above using the compound represented by Formula (4) obtained in the substep (B1).

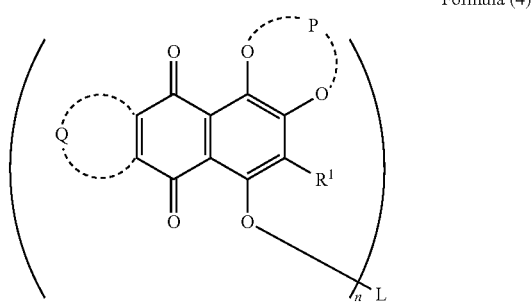

Formula (4)

In Formula (4), P has the same definition as P in Formula (2). Each of $R^1$, L, n and Q in Formula (4) has the same definition as $R^1$, L, n and Q in Formula (1) respectively.

<<Step (B1)>>

In the step (B1), the compound represented by Formula (2) obtained in the step (A) above is subjected to alkylation of a hydroxyl group contained at the 4-position to produce the compound represented by Formula (4).

Preferable examples of the alkylation method applied in the step (B1) include (1) a synthesis method using a phase transfer catalyst such as a tetrabutylammonium salt and the like in a biphase system of an organic phase/an aqueous phase, and (2) a synthesis method using crown ethers under basic conditions, from the viewpoints of economical rationality.

Next, the alkylating agent used in the reaction in the present step will be described.

The alkylating agent used in the present step is a compound having a structure represented by L-$(X)_n$. Here, L has the same definition as L in Formula (1), and a preferable range for L is also the same as that for L in Formula (1). n has the same definition as n in Formula (1). X denotes a halogen atom or an organic sulfonyloxy group. Examples of the halogen atom represented by X include a chlorine atom, a bromine atom, an iodine atom, and the like. Examples of the sulfonyloxy group represented by X include methanesulfonyloxy, benzenesulfonyloxy, p-toluenesulfonyloxy, and the like.

Examples of the alkylating agents include alkyl halides such as n-propyl bromide, n-butyl bromide, n-ethyl iodide, n-butyl iodide, isobutyl bromide, 2-ethylhexyl bromide, n-octyl bromide, 1,3-diiodopropane, 1,4-diiodobutane, 1,6-diiodohexane, 1,8-diiodooctane, 1,3-diiodoperfluoropropane, 1,2,3-tribromopropane, 1,4-diiodoperfluorobutane, 1,6-diiodoperfluorohexane, 1,8-diiodoperfluorooctane and the like; alkyl halides which contain an ether group or a carboxylic acid ester group such as 2-ethoxyethylbromide, methoxyethylbromide, 2-acetyloxyethylbromide, 4-acetoxymethylcyclohexylmethylchloride, 4-acetyloxybutylchloride, 2-(2'-acetoxyethoxy)ethylchloride, and the like; organic sulfonic acid esters which contain an ether group or a carboxylic acid ester group such as 2-ethoxyethyl methanesulfonate, methoxyethyl methanesulfonate, 2-acetyloxyethyl benzenesulfonate, 4-acetoxymethylcyclohexylmethyl methanesulfonate, 4-acetyloxybutyl methanesulfonate, 2-(2'-acetoxyethoxy)ethyl methanesulfonate, and the like; organic sulfonic acid esters which contain an unsaturated bond such as 2-acryloyloxyethyl methanesulfonate, 4-acryloyloxybutyl methanesulfonate, 4-acryloyloxymethylcyclohexylmethyl methanesulfonate, 4-methacryloyloxybutyl methanesulfonate, and the like; alkyl organic sulfonic acid esters which contain a substituted aryl group such as 2-(4'-methoxycarbonylphenoxy)ethyl methanesulfonate, 2-(4'-ethoxycarbonylphenoxy)ethyl methanesulfonate, 2-[2'-(4''-ethoxycarbonylphenoxy)ethoxy]ethyl methanesulfonate, 4-(4'-methoxycarbonylphenoxy)butyl methanesulfonate, 4-(4'-methoxycarbonylphenoxymethyl)cyclohexylmethyl methanesulfonate, and the like; alkyl halides which contain a substituted aryl group such as 2-(4'-methoxycarbonylphenoxy)ethyl bromide, 2-(4'-ethoxycarbonylphenoxy)ethyl bromide, 2-[2'-(4''-ethoxycarbonylphenoxy)ethoxy]ethyl bromide, 4-(4'-methoxycarbonylphenoxy)butyl bromide, 4-(4'-methoxycarbonylphenoxymethyl)cyclohexylmethyl bromide, and the like; and the like. The invention, however, is not limited thereto.

Among these, as the alkylating agent bromide and iodide are particularly preferable, from the viewpoint of the reactivity of raw materials, but these alkylating agents are not easily available and greatly expensive, and accordingly, chloride can be used.

Furthermore, in the case in which it is difficult to obtain alkyl halide itself, the corresponding alcohol is reacted with alkyl or arylsulfonyl chloride such as methane sulfonic acid chloride, p-toluene sulfonylchloride, benzene sulfonylchloride, and the like, and used to derive an alkyl or aryl sulfonic acid ester, which can be used as an alkylating agent.

The reactivity of chloride, or the alkyl or aryl sulfonic acid ester is generally inferior to that of bromide and iodide in many cases, but even when used these alkylating agents, the reactivity can be improved in a case where a phase transfer catalyst of which the anion is bromine or iodine (particularly preferably iodine), is used in a combination with the alkylating agent.

In this regard, the alkylating agent can be arbitrarily selected depending on the priority among availability, cost, and reactivity.

The preferable amount of the alkylating agent used slightly varies depending on the reactivity and the stability of the alkylating agent, but in the case of obtaining the alizarin derivative compound represented by Formula (1) in which n is 1, the amount of the alkylating agent is preferably 1.0 to 2.0 equivalents, and more preferably 1.0 to 1.5 equivalents, with respect to the compound represented by Formula (2). In the case of obtaining the alizarin derivative compound represented by Formula (1) in which n is 2, the amount of the alkylating agent is preferably 0.5 to 1.0 equivalents, and more preferably 0.5 to 0.75 equivalents, with respect to the compound represented by Formula (2). In the case of obtaining the alizarin derivative compound represented by Formula (1) in which n is 3, the amount of the alkylating agent is preferably ⅓ to ⅔ equivalents, and more preferably ⅓ to ½ equivalents, with respect to the compound represented by Formula (2).

For the phase transfer catalysts or crown ethers used in the reaction, the compound group as described above as the phase transfer catalysts and crown ethers which can be used in the step (A) can be preferably used.

The base used in the reaction may be any one of an inorganic base and an organic base, but the inorganic base is preferable. As the inorganic base, alkali metal carbonates (potassium carbonate, sodium carbonate, cesium carbonate, and the like), alkali metal hydroxides (sodium hydroxide, potassium hydroxide, and the like), alkali metal phosphates (trisodium phosphate, tripotassium phosphate, and the like), other metal alkoxides (for example, sodium alkoxide, lithium alkoxide, and the like, and alkoxide derivatives formed in an alcohol solvent), and alkyl metals (for example, methyl lithium, n-butyl lithium, and the like) are preferable, and as the organic base, alkyl amines (triethylamine and the like), organic strong bases (for example, 1,8-diazabicyclo[5,4,0]-7-undecene, 1,5-diazabicyclo[4,3,0]-5-nonene, and the like), and the like are preferable. More preferably, the base is an alkali metal carbonate, an alkali metal hydroxide, or an alkyl amine, and most preferably, an alkali metal carbonate or an alkali metal hydroxide. Further, these bases may be used alone or as a mixture of two or more kinds thereof.

The amount of the inorganic base used in the reaction is preferably 1.0 mole to 5.0 moles, and more preferably 1.0 mole to 2.0 moles, based on 1 mole of the phenolic hydroxyl group contained in the substrate used in the reaction. Further, as the form of the inorganic base used in the reaction, an inorganic base in the form of pellet, an inorganic base in the form of granule, or an inorganic base in the form of powder can be used as it is, but an inorganic base in the form of powder is preferably used as it is.

Regarding these synthesis methods, reference can be made to, for example, "J. Am. Chem. Soc., 1986, vol. 108, p. 7553" and "Organic Preparation and Procedures International, 1999., vol. 31, p. 433."

Furthermore, in the step (B1), a synthesis method for general alkylation of a 1-hydroxy anthraquinone derivative using silver oxide (for example, a method described in Synthesis, 1991, p. 438 as described above) can also be used.

<<Step (B2)>>

In the step (B2), the alizarin derivative compound represented by Formula (1) which is a final product is obtained by deprotection of the compound represented by Formula (4).

In the step (B2), the conditions which are needed to deprotect P in Formula (4) may be any one of acidic conditions, basic conditions, and neutral conditions. Among these conditions, acidic conditions or basic conditions are preferable, and basic conditions are most preferable.

The acid used in the case of carrying out the deprotection under acidic conditions may be any one of an inorganic acid and an organic acid. As the inorganic acid, mineral acids (for example, sulfuric acid, hydrochloric acid, hydrobromic acid, nitric acid, phosphoric acid, and the like) are preferred, and as the organic acid, organic carboxylic acids (for example, acetic acid, oxalic acid, formic acid, propionic acid, benzoic acid, and the like), and sulfonic acids (for example, methanesulfonic acid, ethanesulfonic acid, benzenesulfonic acid, p-toluenesulfonic acid, and the like) are preferably used, and sulfuric acid, hydrochloric acid, acetic acid, and p-toluenesulfonic acid are more preferable, and sulfuric acid and hydrochloric acid are most preferable. In addition, these acids may be used alone or as a mixture of two or more kinds thereof.

The base used in the case of carrying out the deprotection under basic conditions may be any one of an inorganic base and an organic base. As the inorganic base, alkali metal carbonates (potassium carbonate, sodium carbonate, cesium carbonate, and the like), alkali metal hydroxides (sodium hydroxide, potassium hydroxide, and the like), alkali metal phosphates (trisodium phosphate, tripotassium phosphate, and the like), other metal alkoxides (for example, sodium alkoxide, lithium alkoxide, and the like, and alkoxide derivatives formed in an alcohol solvent), and alkyl metals (for example, methyl lithium, n-butyl lithium, and the like) are preferable, and as the organic base, alkyl amines (triethylamine and the like), organic strong bases (for example, 1,8-diazabicyclo[5,4,0]-7-undecene, 1,5-diazabicyclo[4,3,0]-5-nonene, and the like), and the like are preferable. More preferably, the base is an alkali metal carbonate, an alkali metal hydroxide, or an alkyl amine, and most preferably, an alkali metal carbonate or an alkali metal hydroxide. Further, these bases may be used alone or as a mixture of two or more kinds thereof.

In the case of carrying out deprotection under neutral conditions, a hydrogenation method using a metal catalyst and the like, and other methods can be exemplified. For example, the hydrogenation can be carried out at 20° C. to 150° C. and a hydrogen pressure of 0.1 MPa to 10 MPa in the presence of a hydrogenation catalyst. Further, the hydrogenation rate can be suitably determined by changing the amount of the hydrogenation catalyst, the hydrogen pressure during the hydrogenation reaction, the reaction time, and the like.

Examples of the hydrogenation catalyst include compounds containing atoms such as titanium (Ti), vanadium (V), cobalt (Co), nickel (Ni), zirconium (Zr), ruthenium (Ru), rhodium (Rh), palladium (Pd), hafnium (Hf), rhenium (Re), platinum (Pt), and the like.

More specific examples of the hydrogenation catalyst include metallocene-based compounds containing atoms such as Ti, Zr, Hf, Co, Ni, Pd, Pt, Ru, Rh, Re, and the like as described above; a supported type heterogeneous catalyst prepared by causing a metal atom such as Pd, Ni, Pt, Rh, Ru, and the like to be supported on a carrier such as carbon, silica, alumina, diatomaceous earth, and the like; a homogeneous Ziegler catalyst prepared by combining an organic salt or an acetylacetone salt of a metal atom such as Ni, Co, and the like with a reducing agent such as organoaluminum and the like; an organometallic compound or a complex including Ru, Rh, and the like; fullerene or a carbon nanotube that stores hydrogen; and the like.

Among these, the supported type heterogeneous catalyst prepared by causing a metal atom such as Pd, Ni, Pt, Rh, Ru, and the like to be supported on a carrier such as silica, alumina, diatomaceous earth, and the like is preferable from the viewpoint of the reaction efficiency. Further, the supported type heterogeneous catalyst prepared by causing a metal atom such as Pd, Ni, and the like to be supported on a carrier such as silica, alumina, diatomaceous earth, and the like is inexpensive and a particularly useful catalyst in view of industry, which is thus preferable.

The amount of the catalyst used in the reaction is preferably 0.01 mole to 5.0 moles, and more preferably 0.1 mole to 1.0 mole, based on 1 mole of the compound of Formula (4).

For these methods, reference can be made to, for example, the deprotection method described in "Protecting Groups in Organic Synthesis $3^{rd}$ Edition 1999 John Wiley & Sons, Inc."

Any solvent can be usable as the solvent used for the producing method of the exemplary embodiment of the invention, unless the solvent inhibits the reaction in each process. Examples of the solvent include alcohols (for example, methanol, ethanol, propanol, isopropyl alcohol, butanol, sec-butanol, tert-butanol, n-pentanol, n-hexanol, cyclohexanol, 2-methyl-1-pentanol, 1-heptanol, 2-heptanol, 1-octanol, 2-ethylhexanol, benzyl alcohol, ethoxyethanol, propoxyethanol, butoxyethanol, 2-dimethylaminoethanol, 2-methylaminoethanol, ethylene glycol, propylene glycol, 1,4-butanediol); basic organic solvents (for example, methylamine, ethylamine, n-propylamine, isopropylamine, isobutylamine, cyclohexylamine, morpholine, pyrrolidine, piperidine, aniline, 1-aminonaphthalene, pyridine, quinoline, 2-methoxyethyleneamine, ethylenediamine, 1,3-propanediamine, 1,4-butanediamine); phenols (phenol, o-cresol, and the like); alkylthiols (ethanethiol, n-butanethiol, sec-butanethiol, tert-butanethiol, and the like); arylthiols (thiophenol, 4-mercaptopyridine, and the like); ureas (urea, n,n-dimethylimidazolidinone, and the like); aprotic polar solvents (formamide, N,N-dimethylformamide, sulfolane, dimethylsulfoxide, N,N-dimethylacetamide, acetonitrile, N-methylpyrrolidone, and the like); chained or cyclic ethers (for example, diethyl ether, diisopropyl ether, dimethoxyethane, tetrahydrofuran, dioxane, diethylene glycol dimethyl ether); aromatic compounds (for example, toluene, xylene, nitrobenzene, chloronaphthalene, dichlorobenzene); organic acids such as carboxylic acids (for example, acetic acid, propionic acid, trifluoroacetic acid); nitro compounds (for example, nitromethane, nitroethane); esters (for example, ethyl acetate, butyl acetate); ketones (for example, acetone, methyl ethyl ketone); aliphatic hydrocarbons (for example, hexane, octane); alicyclic hydrocarbons (for example, cyclopentane, cyclohexane, methylcyclohexane); halogenohydrocarbons (chloroform, dichloromethane, dichloroethane, carbon tetrachloride, and the like); water; ammonia; a mixture thereof, and the like. Among the above, alcohols such as methanol, ethanol, propanol, butanol, pentanol, 2-dimethylaminoethanol, and ethylene glycol, are preferable. Ethanol, 2-dimethylaminoethanol, and ethylene glycol are more preferable as the solvent. As the solvent for the reaction, water may be used. Further, the reaction may be conducted without the solvent.

In the case of using a solvent, the amount used thereof is preferably 1 fold to 100 folds, and more preferably 3 folds to 50 folds based on the amount by mass of the compounds represented by Formulae (1) to (4).

Further, as for the reaction temperature in the preparation method of the present invention, the optimal temperature varies depending on the kind of the reaction agents used in each of the steps, but the preparation is preferably carried out at −20° C. to 200° C., more preferably −10° C. to 170° C., and most preferably 0° C. to 150° C.

Next, details of each of the compounds such as the alizarin derivative compound represented by Formula (1) above, which is obtained by the preparation method of the present invention, the compound represented by Formula (3) above, which is used as a starting raw material, the compound represented by Formula (2) above, which is produced as an intermediate, and the like will be described.

<Alizarin Derivative Compound Represented by Formula (1)>

The alizarin derivative compound obtained by the preparation method of the present invention is the alizarin derivative compound represented by Formula (1) below.

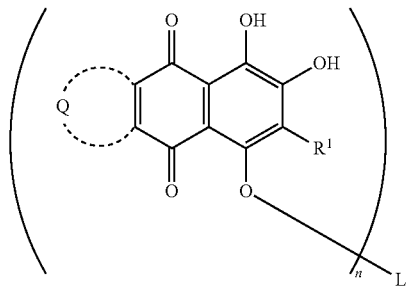

Formula (1)

In Formula (1), $R^1$ represents a hydrogen atom or a substituent. n represents an integer of 1 to 3. When n is 1, L represents $-C(R^{a1})(R^{a2})(R^{a3})$. $R^{a1}$, $R^{a2}$, and $R^{a3}$ each independently represent a hydrogen atom, a substituted or unsubstituted alkyl group having 1 to 30 carbon atoms, or a substituted or unsubstituted aryl group having 6 to 30 carbon atoms. Here, at least one of $R^{a1}$, $R^{a2}$, and $R^{a3}$ represents a substituted or unsubstituted alkyl group having 1 to 30 carbon atoms, or a substituted or unsubstituted aryl group having 6 to 30 carbon atoms. When n is 2, L represents a substituted or unsubstituted divalent linkage group having 2 to 20 carbon atoms. When n is 3, L represents a substituted or unsubstituted trivalent linkage group having 2 to 30 carbon atoms. Q represents an atomic group which is needed to form an aromatic ring or a heteroaromatic ring with adjacent carbon atoms.

In Formula (1), $R^1$ represents a hydrogen atom or a substituent. Examples of the substituent include a halogen atom, cyano group, alkyl group (including a cycloalkyl group, and a bicycloalkyl group), alkenyl group (including a cycloalkenyl group), alkinyl group, aryl group, heterocyclic group, cyano group, hydroxyl group, nitro group, carboxyl group, alkoxy group, aryloxy group, silyloxy group, heterocyclic oxy group, acyloxy group, carbamoyloxy group, alkoxycarbonyloxy group, aryloxycarbonyloxy group, amino group (including an anilino group), acylamino group, aminocarbonylamino group, alkoxycarbonylamino group, aryloxycarbonylamino group, sulfamoylamino group, alkyl or arylsulfonylamino group, mercapto group, alkylthio group, arylthio group, heterocyclic thio group, sulfamoyl group, sulfo group, alkyl or arylsulfinyl group, alkyl or arylsulfonyl group, acyl group, aryloxycarbonyl group, alkoxycarbonyl group, carbamoyl group, aryl or heterocyclic azo group, imide group, phosphino group, phosphinyl group, phosphinyloxy group, phosphinylamino group and silyl group.

Further in detail, $R^1$ represents a hydrogen atom, a halogen atom (for example, a chlorine atom, a bromine atom, or an iodine atom), a cyano group, an alkyl group [which may be a substituted or unsubstituted, and linear, branched, or cyclic alkyl group; an alkyl group (preferably, an alkyl group having 1 to 30 carbon atoms; for example, methyl, ethyl, n-propyl, isopropyl, t-butyl, n-octyl, eicosyl, 2-chloroethyl, 2-cyanoethyl, and 2-ethylhexyl), a cycloalkyl group (preferably, a substituted or unsubstituted cycloalkyl group having 3 to 30 carbon atoms; for example, cyclohexyl, cyclopentyl, and 4-n-dodecylcyclohexyl), a bicycloalkyl group (preferably, a substituted or unsubstituted bicycloalkyl group having 5 to 30 carbon atoms, namely, a monovalent group obtained by removing one hydrogen atom from bicycloalkane having 5 to 30 carbon atoms; for example, bicyclo[1,2,2]heptan-2-yl and bicyclo[2,2,2]octan-3-yl), and further a tricyclo structure having many cyclic structures, and the like; an alkyl group included in a substituent described below (for example, an alkyl group in an alkylthio group) also represents the alkyl group of this concept, an alkenyl group [which may be a substituted or unsubstituted, and linear, branched, or cyclic alkenyl group; an alkenyl group (preferably, a substituted or unsubstituted alkenyl group having 2 to 30 carbon atoms; for example, vinyl, allyl, prenyl, geranyl, and oley), a cycloalkenyl group (preferably, a substituted or unsubstituted cycloalkenyl group having 3 to 30 carbon atoms, namely, a monovalent group obtained by removing one hydrogen atom from cycloalkene having 3 to 30 carbon atoms; for example, 2-cyclopenten-1-yl and 2-cyclohexen-1-yl), a bicycloalkenyl group (a substituted or unsubstituted bicycloalkenyl group, and preferably, a substituted or unsubstituted bicycloalkenyl group having 5 to 30 carbon atoms, namely, a monovalent group obtained by removing one hydrogen atom from bicycloalkene having one double bond; for example, bicyclo[2,2,1]hepto-2-en-1-yl and bicyclo[2,2,2]octo-2-en-4-yl)], an alkynyl group (preferably, a substituted or unsubstituted alkynyl group having 2 to 30 carbon atoms; for example, ethynyl, propargyl, and a trimethylsilylethynyl group), an aryl group (preferably, a substituted or unsubstituted aryl group having 6 to 30 carbon atoms; for example, phenyl, p-tolyl, naphthyl, m-chlorophenyl, and o-hexadecanoylaminophenyl), a heterocyclic group (preferably, a monovalent group obtained by removing one hydrogen atom from 5- or 6-membered, substituted or unsubstituted, aromatic or non-aromatic heterocyclic compound, and more preferably a 5- or 6-membered aromatic heterocyclic group having 3 to 30 carbon atoms; for example, 2-furyl, 2-thienyl, 2-pyrimidinyl, and 2-benzothiazolyl), a hydroxy group, a nitro group, a carboxy group, an alkoxy group (preferably, a substituted or unsubstituted alkoxy group having 1 to 30 carbon atoms; for example, methoxy, ethoxy, isopropoxy, t-butoxy, n-octyloxy, and 2-methoxyethoxy), an aryloxy group (preferably, a substituted or unsubstituted aryloxy group having 6 to 30 carbon atoms; for example, phenoxy, 2-methylphenoxy, 4-t-butylphenoxy, 3-nitrophenoxy, and 2-tetradecanoylaminophenoxy), a silyloxy group (preferably, a silyloxy group having 3 to 20 carbon atoms; for example, trimethylsilyloxy and t-butyldimethylsilyloxy), a heterocyclic oxy group (preferably, a substituted or unsubstituted heterocyclic oxy group having 2 to 30 carbon atoms; for example, 1-phenyltetrazole-5-oxy and 2-tetrahydropyranyloxy), an acyloxy group (preferably, a formyloxy group, a substituted or unsubstituted alkylcarbonyloxy group having 2 to 30 carbon atoms, or a substituted or unsubstituted arylcarbonyloxy group having 6 to 30 carbon atoms; for example, formyloxy, acetyloxy, pivaloyloxy, stearoyloxy, benzoyloxy, and p-methoxyphenylcarbonyloxy), a carbamoyloxy group (preferably, a substituted or unsubstituted carbamoyloxy group having 1 to 30 carbon atoms; for example, N,N-dimethylcarbamoyloxy, N,N-diethylcarbamoyloxy, morpholinocarbonyloxy, N,N-di-n-octylaminocarbonyloxy, and N-n-octylcarbamoyloxy), an alkoxycarbonyloxy group (preferably, a substituted or unsubstituted alkoxycarbonyloxy group having 2 to 30 carbon atoms; for example, methoxycarbonyloxy, ethoxycarbonyloxy, t-butoxycarbonyloxy, and n-octylcarbonyloxy), an aryloxycarbonyloxy group (preferably, a substituted or unsubstituted aryloxycarbonyloxy group having 7 to 30 carbon atoms; for example, phenoxycarbonyloxy, p-methoxyphenoxycarbonyloxy, and p-n-hexadecyloxyphenoxycarbonyloxy), an amino group (preferably, an amino group, a substituted or unsubstituted alkylamino group having 1 to 30 carbon atoms, or a substituted or unsubstituted anilino group having 6 to 30 carbon atoms; for example, amino, methylamino, dimethylamino, anilino, N-methyl-anilino, and diphenylamino), an acylamino group (preferably, a formylamino group, a substituted or unsubstituted alkylcarbonylamino group having 1 to 30 carbon atoms, or a substituted or unsubstituted arylcarbonylamino group having 6 to 30 carbon atoms; for example, formylamino, acetylamino, pivaloylamino, lauroylamino, benzoylamino, and 3,4,5-tri-n-octyloxyphenylcarbonylamino), an aminocarbonylamino group (preferably, a substituted or unsubstituted aminocarbonylamino group having 1 to 30 carbon atoms; for example, carbamoylamino, N,N-dimethylaminocarbonylamino, N,N-diethylaminocarbonylamino, and morpholinocarbonylamino), an alkoxycarbonylamino group (preferably, a substituted or unsubstituted alkoxycarbonylamino group having 2 to 30 carbon atoms; for example, methoxycarbonylamino, ethoxycarbonylamino, t-butoxycarbonylamino, n-octadecyloxycarbonylamino, and N-methyl-methoxycarbonylamino), an aryloxycarbonylamino group (preferably, a substituted or unsubstituted aryloxycarbonylamino group having 7 to 30 carbon atoms; for example, phenoxycarbonylamino, p-chlorophenoxycarbonylamino, and m-n-octyloxyphenoxycarbonylamino), a sulfamoylamino group (preferably, a substituted or unsubstituted sulfamoylamino group having 0 to 30 carbon atoms; for example, sulfamoylamino, N,N-dimethylaminosulfonylamino, and N-n-octylaminosulfonylamino), an alkylsulfonylamino group and an arylsulfonylamino group (preferably, a substituted or unsubstituted alkylsulfonylamino group having 1 to 30 carbon atoms and a substituted or unsubstituted arylsulfonylamino group having 6 to 30 carbon atoms; for example, methylsulfonylamino, butylsulfonylamino, phenylsulfonylamino, 2,3,5-trichlorophenylsulfonylamino, and p-methylphenylsulfonylamino), a mercapto group, an alkylthio group (preferably, a substituted or unsubstituted alkylthio group having 1 to 30 carbon atoms; for example, methylthio, ethylthio, and n-hexadecylthio), an arylthio group (preferably, a substituted or unsubstituted arylthio group having 6 to 30 carbon atoms; for example, phenylthio, p-chlorophenylthio, and m-methoxyphenylthio), a heterocyclic thio group (preferably, a substituted or unsubstituted heterocyclic thio group having 2 to 30 carbon atoms; for example, 2-benzothiazolylthio and 1-phenyltetrazol-5-ylthio), a sulfamoyl group (preferably, a substituted or unsubstituted sulfamoyl group having 0 to 30 carbon atoms; for example, N-ethylsulfamoyl, N-(3-dodecyloxypropyl)sulfamoyl, N,N-dimethylsulfamoyl, N-acetylsulfamoyl, N-benzoylsulfamoyl, and N—(N'-phenylcarbamoyl)sulfamoyl), a sulfo group, an alkylsulfinyl group and an arylsulfinyl group (preferably, a substituted or unsubstituted alkylsulfinyl group having 1 to 30 carbon atoms and a substituted or unsubstituted arylsulfinyl group having 6 to 30 carbon atoms; for example, methylsulfinyl, ethylsulfinyl, phenylsulfinyl, and p-methylphenylsulfinyl), an alkylsulfonyl group and an arylsulfonyl group (preferably, a substituted or unsubstituted alkylsulfonyl group having 1 to 30 carbon atoms and a substituted or unsubstituted arylsulfonyl group having 6 to 30 carbon atoms; for example, methylsulfonyl, ethylsulfonyl, phenylsulfonyl, and p-methylphenylsulfonyl), an acyl group (preferably, a formyl group, a substituted or unsubstituted alkylcarbonyl group having 2 to 30 carbon atoms, a substituted or unsubstituted arylcarbonyl group having 7 to 30 carbon atoms, or a substituted or unsubstituted heterocyclic carbonyl group having 4 to 30 carbon atoms in which the heterocycle bonds to the carbonyl group through a carbon atom; for example, acetyl, pivaloyl, 2-chloroacetyl, stearoyl, benzoyl, p-n-octyloxyphenylcarbonyl, 2-pyridylcarbonyl, and 2-furylcarbonyl), an aryloxycarbonyl group (preferably, a substituted or unsubstituted aryloxycarbonyl group having 7 to 30 carbon atoms; for example, phenoxycarbonyl, o-chlorophenoxycarbonyl, m-nitrophenoxycarbonyl, and p-t-butylphenoxycarbonyl), an alkoxycarbonyl group (preferably, a substituted or unsubstituted alkoxycarbonyl group having 2 to 30 carbon atoms; for example, methoxycarbonyl, ethoxycarbonyl, t-butoxycarbonyl, and n-octadecyloxycarbonyl), a carbamoyl group (preferably, a substituted or unsubstituted carbamoyl group having 1 to 30 carbon atoms; for example, carbamoyl, N-methylcarbamoyl, N,N-dimethylcarbamoyl, N,N-di-n-octylcarbamoyl, and N-(methylsulfonyl)carbamoyl), an arylazo group and a heterocyclic azo group (preferably, a substituted or unsubstituted arylazo group having 6 to 30 carbon atoms and a substituted or unsubstituted heterocyclic azo group having 3 to 30 carbon atoms; for example, phenylazo, p-chlorophenylazo, and 5-ethylthio-1,3,4-thiadiazol-2-ylazo), an imido group (for example, N-succinimide and N-phthalimide), a phosphino group (preferably, a substituted or unsubstituted phosphino group having 2 to 30 carbon atoms; for example, dimethylphosphino, diphenylphosphino, and methylphenoxyphosphino), a phosphinyl group (preferably, a substituted or unsubstituted phosphinyl group having 2 to 30 carbon atoms; for example, phosphinyl, dioctyloxyphosphinyl, and diethoxyphosphinyl), a phosphinyloxy group (preferably, a substituted or unsubstituted phosphinyloxy group having 2 to 30 carbon atoms; for example, diphenoxyphosphinyloxy and dioctyloxyphosphinyloxy), a phosphinylamino group (preferably, a substituted or unsubstituted phosphinylamino group having 2 to 30 carbon atoms; for example, dimethoxyphosphinylamino and dimethylaminophosphinylamino), a silyl group (preferably, a substituted or unsubstituted silyl group having 3 to 30 carbon atoms; for example, trimethylsilyl, t-butyldimethylsilyl, and phenyldimethylsilyl.

Among the functional groups described above, the group which has a hydrogen atom may be further substituted by the above group after removing the hydrogen atom. Examples of such functional group include an alkylcarbonylaminosulfonyl group, an arylcarbonylaminosulfonyl group, an alkylsulfonylaminocarbonyl group, and an arylsulfonylaminocarbonyl group. Specific examples thereof include methylsulfonylaminocarbonyl, p-methylphenylsulfonylaminocarbonyl, acetylaminosulfonyl, and a benzoylaminosulfonyl group. The group represented by $R^1$ may be further substituted with a substituent.

A hydrogen atom, a substituted or unsubstituted alkyl group, a substituted or un substituted phenyl group, a substituted or un substituted alkoxy group, and a substituted or un substituted heterocyclic group are preferable, a hydrogen atom, and a substituted or unsubstituted alkyl group are more preferable, and a hydrogen atom is even more preferable, as the group represented by $R^1$.

Q represents an atomic group which is needed to form an aromatic ring or a heteroaromatic ring with adjacent carbon atoms.

The aromatic hydrocarbon ring group or heteroaromatic ring group formed with the atom group represented by Q is preferably a 4- to 10-membered ring group, more preferably a 5- to 7-membered ring group, even more preferably a 5- or 6-membered ring group, and particularly preferably a 6-membered ring group.

The heteroaromatic ring group formed with the atom group represented by Q is not particularly limited, but it is preferably a heteroaromatic ring group containing a hetero atom selected from the group consisting of a nitrogen atom, an oxygen atom, a sulfur atom, a selenium atom, a silicon atom, a germanium atom, and a phosphorus atom, more preferably a heteroaromatic ring group containing a hetero atom selected from the group consisting of nitrogen, oxygen, and sulfur, and particularly preferably a nitrogen-containing heteroaromatic ring group.

The number of the hetero atoms contained in one heteroaromatic ring group formed with the atom group represented by Q is not particularly limited, but it is preferably 1 to 3.

Examples of the aromatic or heteroaromatic ring which derive an aromatic hydrocarbon ring group or a heteroaromatic ring group including the atomic group represented by Q, include a benzene ring, a pyridine ring, a pyrazine ring, a pyrimidine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring, a phosphole ring, and the like.

Furthermore, the aromatic hydrocarbon ring group or heteroaromatic ring group formed with the atomic group represented by Q may further contain a substituent, and as the substituent, those exemplified above represented by $R^1$ can be applied herein.

Furthermore, the aromatic ring or heteroaromatic ring from which the aromatic hydrocarbon ring group or heteroaromatic ring group formed with the atom group represented by Q may be derived may further form a condensed ring with other rings, and examples of the condensed ring formed include a benzene ring, a pyridine ring, a pyrazine ring, a pyrimidine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring, a phosphole ring, and the like.

The substituent and condensed ring may further contain a substituent and may even further be condensed with other rings. As the substituent, those exemplified above represented by $R^1$ may be applied.

The aromatic or heteroaromatic ring which derives an aromatic hydrocarbon ring group or a heteroaromatic ring group including the atomic group represented by Q, is preferably a benzene ring, a pyridine ring, a pyrazine ring, a pyrimidine ring, a triazine ring, a pyrrole ring, a pyrazole ring, an imidazole ring, a triazole ring, an oxazole ring, a thiazole ring, a furan ring, or a thiophene ring; more preferably a benzene ring, a pyridine ring, a pyrazine ring, a pyrrole ring, a pyrazole ring, an imidazole ring, an oxazole ring, a thiazole ring, or a thiophene ring; and particularly preferably a benzene ring, a pyridine ring, or a pyrazine ring.

In Formula (1), n represents an integer of 1 to 3. n is preferably 1 or 2, and more preferably 1.

When n is 1, L represents —$C(R^{a1})(R^{a2})(R^{a3})$. $R^{a1}$, $R^{a2}$, and $R^{a3}$ each independently represent a hydrogen atom, a substituted or unsubstituted alkyl group having 1 to 30 carbon atoms, or a substituted or unsubstituted aryl group having 6 to 30 carbon atoms. Here, at least one of $R^{a1}$, $R^{a2}$, and $R^{a3}$ represents a substituted or unsubstituted alkyl group having 1 to 30 carbon atoms, or a substituted or unsubstituted aryl group having 6 to 30 carbon atoms. When n is 2, L represents a substituted or unsubstituted divalent linkage group having 2 to 20 carbon atoms. When n is 3, L represents a substituted or unsubstituted trivalent linkage group having 2 to 30 carbon atoms.

Examples of the substituted or unsubstituted alkyl group represented by $R^{a1}$, $R^{a2}$, or $R^{a3}$ having 1 to 30 carbon atoms include a substituted or unsubstituted straight chain alkyl group having 1 to 30 carbon atoms (for example, methyl, ethyl, n-propyl, isopropyl, t-butyl, n-octyl, eicosyl, 2-chloroethyl, 2-cyanoethyl, and 2-ethylhexyl); a substituted or unsubstituted cycloalkyl group having 3 to 30 carbon atoms (for example, cyclohexyl, cyclopentyl, and 4-n-dodecylcyclohexyl); a substituted or unsubstituted bicycloalkyl group having 5 to 30 carbon atoms (namely, a monovalent group obtained by removing one hydrogen atom from a bicycloalkane having 5 to 30 carbon atoms; for example, bicyclo[1,2,2]heptan-2-yl and bicyclo[2,2,2]octan-3-yl); and an alkyl group having a tricyclo structure and 5 to 30 carbon atoms.

Examples of the substituted or unsubstituted aryl group represented by $R^{a1}$, $R^{a2}$ or $R^{a3}$ having 6 to 30 carbon atoms include a phenyl group, a p-tolyl group, a naphthyl group, a m-chlorophenyl group, and an o-hexadecanoylaminophenyl group.

Example of a substituent which may be substituted on the group represented by $R^{a1}$, $R^{a2}$ or $R^{a3}$ includes the group described for $R^1$. The substitutent preferably includes a halogen atom, a cyano group, an alkoxy group, a hydroxyl group, an alkoxycarbonyloxy group, and an alkoxycarbonylamino group, and most preferably an alkoxy group.

At least one group represented by $R^{a1}$, $R^{a2}$ or $R^{a3}$ is a substituted or unsubstituted alkyl group having 1 to 30 carbon atoms, or a substituted or unsubstituted aryl group having 6 to 30 carbon atoms. It is preferable that two groups among the groups represented by $R^{a1}$, $R^{a2}$ and $R^{a3}$ are hydrogen atoms, and one remaining group among the groups represented by $R^{a1}$, $R^{a2}$ and $R^{a3}$ is a substituted or unsubstituted alkyl group having 1 to 30 carbon atoms.

When n is 2, L represents a substituted or unsubstituted divalent linking group having 2 to 20 carbon atoms, more preferably 2 to 15 carbon atoms, and most preferably 2 to 10 carbon atoms.

The divalent linking group represented by L is an atom group formed with at least one selected from a carbon atom, a hydrogen atom, a nitrogen atom, a sulfur atom, and an oxygen atom, and examples thereof include those having 2 to 20 carbon atoms. Specific examples of L include an alkylenyl group (a methylenyl group, an ethylenyl group, a propylenyl group, and the like), a cycloalkylenyl group (a cyclohexylene group and the like), an alkenylenyl group (a vinylenyl group, a dimethyl vinylenyl group, and the like), an alkynylenyl group (ethynylenyl group and the like), an arylenyl group (a phenylenyl group and a naphthalenediyl group), and a heteroarylenyl group (a pyridinediyl group, a thiophenediyl group, and the like). Further, the L may have linkage of carbon chains with groups such as an oxy group (—O—), a thio group (—S—), —NH—, an imino group (—NR—) (a phenylimino group and the like), —N=, —CO—, —SO$_2$—, a phosphinidenyl group (—PR—) (a phenylphosphinidenyl group, and the like), a silylenyl group (—SiRR'—) (a dimethylsilylenyl group, a diphenylsilylenyl group, and the like), and the like. (Herein, R and R' each represent an alkyl group or an aryl group.)

Moreover, this divalent linking group may have a substituent, and examples of the substituent include an alkyl group (a methyl group, an ethyl group, and the like), an acetoxy group (a methoxy group, an ethoxy group, and the like), and the like.

Further, L may be formed with combinations of two or more of the above-mentioned divalent linking groups. Preferable examples of the combination include -(arylene)-COO—, —(arylene)-CONH—, -(alkylene)-SO$_2$NH—, -(alkylene)-OCONH—, -(arylene)-NHCONH—, -(alkylene)-NHSO$_2$NH—, -(alkylene)-CONH—, -(arylene)-SO$_2$NH—, —COO-(alkylene)-, —CONH-(alkylene)-, —SO$_2$NH-(alkylene)-, —NHCONH-(alkylene)-, —CO-(alkylene)-, —O-(alkylene)-, -(alkylene)-NHCONH—, —S-(alkylene)-, and the like.

When n is 3, L represents a substituted or unsubstituted linking group having 2 to 30 carbon atoms, more preferably 2 to 25 carbon atoms, and most preferably 2 to 20 carbon atoms.

Examples of the trivalent linking group represented by L include those exemplified with respect to the group obtained by removal of one substituent (which may be a hydrogen atom) from the linking group exemplified with respect to the divalent linking group.

One of the more preferable embodiments of the alizarin derivative compound represented by Formula (1) is an alizarin derivative compound represented by the following Formula (5) (the alizarin derivative compound of the present invention) which is a novel compound.

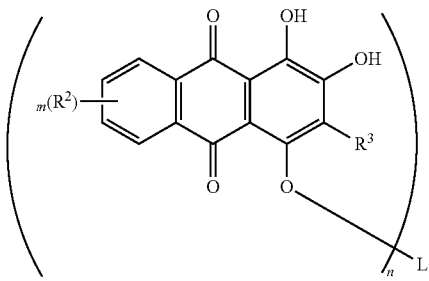

Formula (5)

In Formula (5), $R^2$ represents a hydrogen atom, a substituted or unsubstituted alkyl group having 1 to 30 carbon atoms, a substituted or unsubstituted aryl group having 6 to 30 carbon atoms, or a substituted or unsubstituted alkoxy group having 1 to 30 carbon atoms. m represents an integer of 0 to 4. $R^3$ represents a hydrogen atom, a substituted or unsubstituted alkyl group having 1 to 30 carbon atoms, a substituted or unsubstituted aryl group having 6 to 30 carbon atoms, or a substituted or unsubstituted alkoxy group having 1 to 30 carbon atoms. n represents an integer of 1 to 3. When n is 1, L represents —C($R^{a1}$)($R^{a2}$)($R^{a3}$). $R^{a1}$, $R^{a2}$, and $R^{a3}$ each independently represent a hydrogen atom, a substituted or unsubstituted alkyl group having 1 to 30 carbon atoms, or a substituted or unsubstituted aryl group having 6 to 30 carbon atoms. Here, at least one of $R^{a1}$, $R^{a2}$, and $R^{a3}$ represents a substituted or unsubstituted alkyl group having 1 to 30 carbon atoms, or a substituted or unsubstituted aryl group having 6 to 30 carbon atoms. When n is 2, L represents a substituted or unsubstituted divalent linkage group having 2 to 20 carbon atoms. When n is 3, L represents a substituted or unsubstituted trivalent linkage group having 2 to 30 carbon atoms.

In Formula (5), a substituted or unsubstituted alkyl group represented by $R^2$ having 1 to 30 carbon atoms has the same definitions as the group in a case where $R^1$ in Formula (1) represents a substituted or unsubstituted alkyl group having 1 to 30 carbon atoms. Examples of a substituted or unsubstituted aryl group represented by $R^2$ having 6 to 30 carbon atoms include a phenyl group, a naphthyl group and an anthranyl group. A substituted or unsubstituted aryl group represented by $R^2$ having 6 to 30 carbon atoms is preferably a phenyl group. A substituted or unsubstituted alkoxy group represented by $R^2$ having 1 to 30 carbon atoms has the same definitions as the group in a case where $R^1$ in Formula (1) represents a substituted or unsubstituted alkoxy group having 1 to 30 carbon atoms.

The group represented by $R^2$ is most preferably a substituted or unsubstituted alkyl group having 1 to 30 carbon atoms.

In Formula (5), m represents an integer of 0 to 4. m is preferably 0, 1 or 2, and most preferably 0.

In Formula (5), $R^3$ represents a hydrogen atom, a substituted or unsubstituted alkyl group having 1 to 30 carbon atoms, a substituted or unsubstituted aryl group having 6 to 30 carbon atoms, or a substituted or unsubstituted alkoxy group having 1 to 30 carbon atoms.

Examples of the substituted or unsubstituted alkyl group represented by $R^3$ having 1 to 30 carbon atoms include a substituted or unsubstituted straight chain alkyl group having 1 to 30 carbon atoms (for example, methyl, ethyl, n-propyl, isopropyl, t-butyl, n-octyl, eicosyl, 2-chloroethyl, 2-cyanoethyl, and 2-ethylhexyl); a substituted or unsubstituted cycloalkyl group having 3 to 30 carbon atoms (for example, cyclohexyl, cyclopentyl, and 4-n-dodecylcyclohexyl); a substituted or unsubstituted bicycloalkyl group having 5 to 30 carbon atoms (namely, a monovalent group obtained by removing one hydrogen atom from a bicycloalkane having 5 to 30 carbon atoms; for example, bicyclo[1,2,2]heptan-2-yl and bicyclo[2,2,2]octan-3-yl); and an alkyl group having a tricyclo structure and 5 to 30 carbon atoms.

Examples of the substituted or unsubstituted aryl group represented by $R^3$ having 6 to 30 carbon atoms include a phenyl group, a p-tolyl group, a naphthyl group, a m-chlorophenyl group, and an o-hexadecanoylaminophenyl group.

Examples of the substituted or unsubstituted alkoxy group represented by $R^3$ having 1 to 30 carbon atoms include a methoxy group, an ethoxy group, an isopropoxy group, a t-butoxy group, a n-octyloxy group, and a 2-methoxyethoxy group.

The group represented by $R^3$ is preferably a hydrogen atom.

An even more preferable embodiment of the alizarin derivative compound represented by Formula (5) is an alizarin derivative compound represented by the following Formula (6).

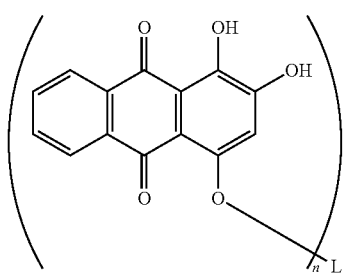

Formula (6)

In Formula (6), n and L have the same definition as n and L in Formula (5) above, respectively, and each preferable range for n and L is also the same as that for n and L in Formula (5) above, respectively.

<Compound Represented by Formula (3)>

The compound represented by the following Formula (3) is a compound used as a starting material in the preparation method of the present invention.

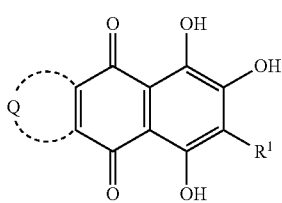

Formula (3)

In Formula (3), $R^1$ and Q have the same definition as $R^1$ and Q in Formula (1) above, respectively, and each preferable range for $R^1$ and Q is also the same as that for $R^1$ and Q in Formula (1) above, respectively.

<Compound Represented by Formula (2) and Compound Represented by Formula (4)>

The compound represented by the following Formula (2) and the compound represented by Formula (4) below are compounds produced as intermediates in the preparation method of the present invention.

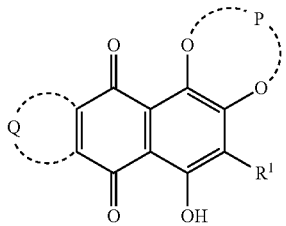

Formula (2)

In Formula (2), P represents an atomic group which includes an atom(s) selected from a hydrogen atom, a carbon atom, an oxygen atom, a sulfur atom, a silicon atom and a boron atom, and which is needed to form a ring structure group with adjacent two oxygen atoms and two carbon atoms. Each of $R^1$ and Q has the same definition as $R^1$ and Q in Formula (1) respectively, and an each preferable range for $R^1$ and Q is also the same as that for $R^1$ and Q in Formula (1) respectively.

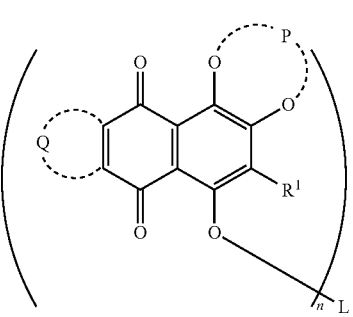

Formula (4)

In Formula (4), P has the same definition as P in Formula (2), and a preferable range for P is also the same as that for P in Formula (2). Each of $R^1$, L, n and Q has the same definition as $R^1$, L, n and Q in Formula (1) respectively, and an each preferable range for $R^1$, L, n and Q is also the same as that for $R^1$, L, n and Q in Formula (1) respectively.

In Formula (2) or Formula (4), P represents an atomic group which includes an atom(s) selected from a hydrogen atom, a carbon atom, an oxygen atom, a sulfur atom, a silicon atom and a boron atom, and which is needed to form a ring structure group with adjacent two oxygen atoms and two carbon atoms. An atom which is included in the atomic group is more preferably a carbon atom, a silicon atom, a sulfur atom, or a boron atom, and most preferably a carbon atom or a silicon atom.

As described above, a heavy metal atom is not included in the atoms constituting the atom group represented by P in view of low preparative costs (a step of removing a heavy metal atom is not required and a raw material compound is easily available) and reduced environmental load can be accomplished by having the atom group represented by P not included with a heavy metal atom, which is thus favorable.

The ring structure formed by the atom group represented by P and two adjacent oxygen atoms is preferably a 5-membered ring or a 6-membered ring, and more preferably a 5-membered ring. The ring structure functions as a protecting group of a cathecol moiety in the preparation method of the present invention.

The ring structure formed by the atom group represented by P and an adjacent oxygen atom will be described in more detail.

<Ring Structure (1): Ring Structure Formed by Carbon Atom Contained in P together with Two Adjacent Oxygen Atoms>

In one embodiment of the ring structures (1), an embodiment in which P represented by =C($R^4$)($R^5$) forms a ring structure represented by the following Formula (7) can be exemplified.

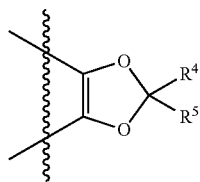

Formula (7)

In Formula (7), $R^4$ and $R^5$ each independently represent a hydrogen atom or a substituent, and examples of the substituents include the substituents represented by $R^1$ in Formula (1) above.

Most preferably, $R^4$ and $R^5$ are both hydrogen atoms (specifically, an embodiment in which a methylene acetal is formed), a substituted or unsubstituted alkyl group (specifically, an embodiment in which an isopropylidene acetal, a cyclohexylidene acetal, a benzylidene acetal, or the like is formed), a substituted or unsubstituted phenyl group (specifically, an embodiment in which a diphenylmethylene acetal, a 4-methoxyphenylmethylene acetal, or the like is formed), and an embodiment in which a substituted or unsubstituted alkoxy group is adopted, or an embodiment in which $R^4$ and $R^5$ each independently adopt a hydrogen atom, a substituted or unsubstituted alkyl group, a substituted or unsubstituted phenyl group, and a substituted or unsubstituted alkoxy group (specifically, an embodiment in which 2-ethoxy-2-methylbenzo-1,3-dioxolane, 2-ethoxy-2-ethylbenzo-1,3-dioxolane, 2-ethoxy-2-propylbenzo-1,3-dioxolane, or the like is formed), and the like.

As other embodiments of the ring structure (1), an embodiment in which P represented by a carbonyl group (=CO) forms a ring structure represented by the following Formula (8) can be exemplified.

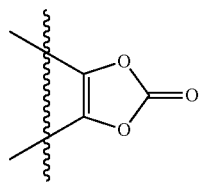

Formula (8)

<Ring Structure (2): Ring Structure Formed by Silicon Atom Contained in P together with Two Adjacent Oxygen Atoms>

As one of the embodiments of the ring structure (2), an embodiment in which P represented by =Si($R^4$)($R^5$) forms a ring structure represented by the following Formula (9) can be exemplified.

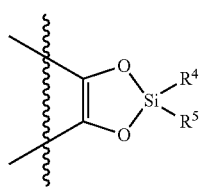

Formula (9)

In Formula (9), $R^4$ and $R^5$ each independently represent a hydrogen atom or a substituent, and examples of the substituent include the substituents represented by $R^1$ in Formula (1) above.

In Formula (9), $R^4$ and $R^5$ are more preferably an alkyl group, a cycloalkyl group, or an aryl group.

As other embodiments of the ring structure (2), an embodiment in which P represented by —Si($R^6$)($R^7$)—O—Si($R^8$)($R^9$)— forms a ring structure together with two adjacent oxygen atoms can also be exemplified. Herein, $R^6$ to $R^9$ each independently represent a substituent, and examples of the substituents include the substituents represented by $R^1$ in Formula (1) above.

<Ring Structure (3): Ring Structure Formed by Sulfur Atom Contained in P together with Two Adjacent Oxygen Atoms>

A case in which P is an atom group which forms a ring through a sulfur atom is a case in which P is represented by S, SO, or $SO_2$, preferably a case in which P is represented by SO or $SO_2$, and most preferably an embodiment in which P represented by SO forms a ring structure represented by the following Formula (10).

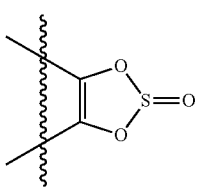

Formula (10)

<Ring Structure (4): Ring Structure Formed by Boron Atom Contained in P together with Two Adjacent Oxygen Atom>

As the ring structure (4), an embodiment in which P represented by =B($R^4$)($R^5$) or =$BR^4$ forms a ring structure represented by the following Formula (11) or (12) can be exemplified.

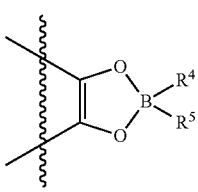

Formula (11)

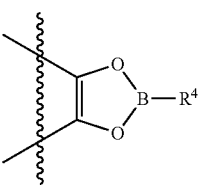

Formula (12)

In Formula (11) or (12), $R^4$ and $R^5$ each independently represent a substituent and examples of the substituent include the substituents represented by $R^1$ in Formula (1) above.

In Formula (11), $R^4$ and $R^5$ are more preferably an aryl group, an alkyl group, or a hydroxyl group. In Formula (12), $R^4$ is even more preferably an aryl group, an alkyl group, or a hydroxyl group.

Hereinbelow, specific examples of the alizarin derivative compound (the alizarin derivative compound of the present invention) obtained by the preparation method of the present invention are presented, but the present invention is not limited thereto.

B-1 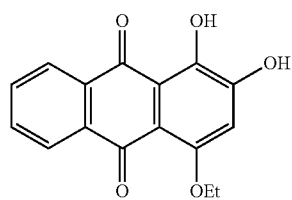 B-2 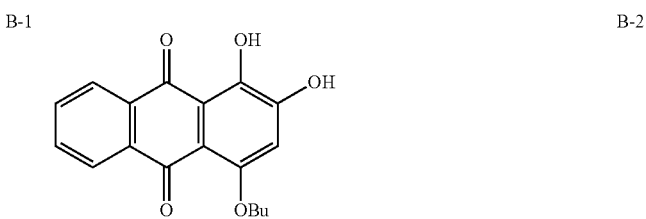
B-3 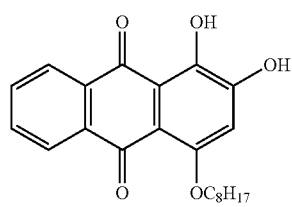 B-4 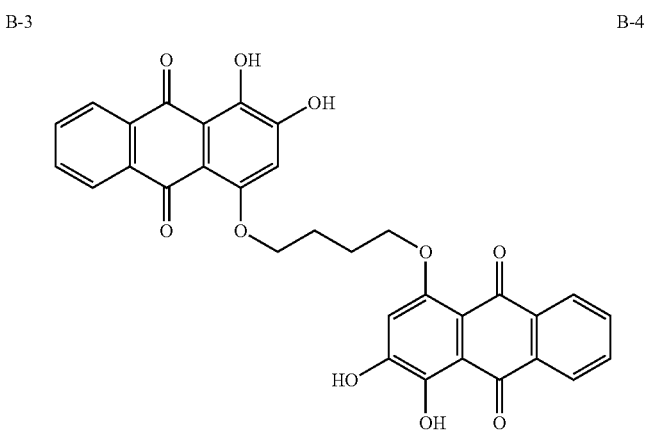
B-5 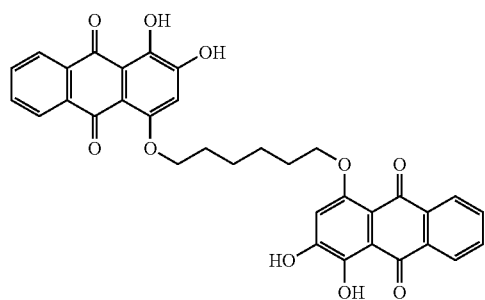 B-6
B-7 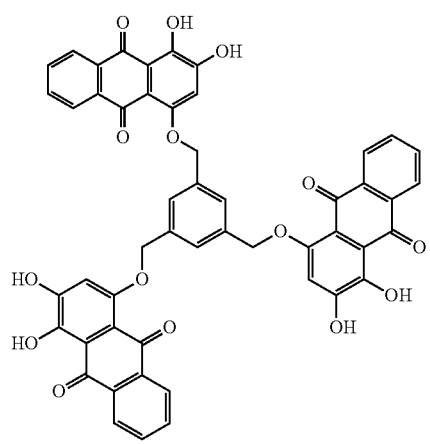 B-8 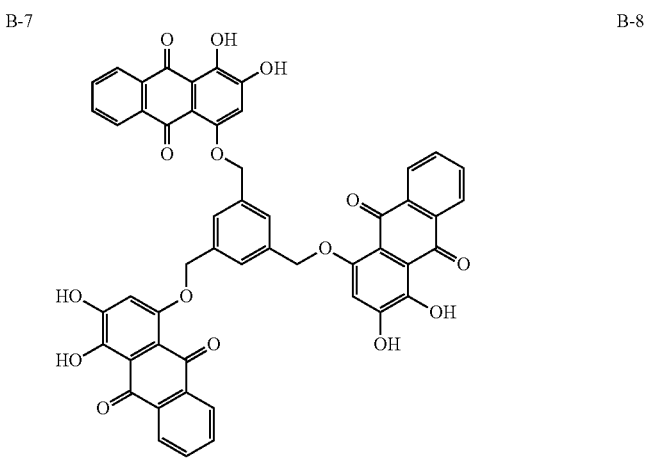

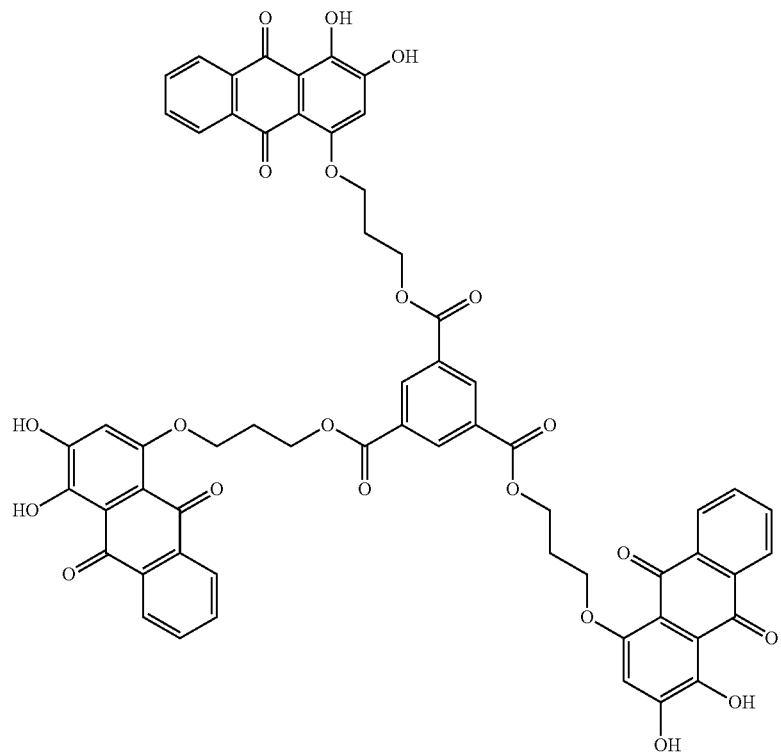
B-9
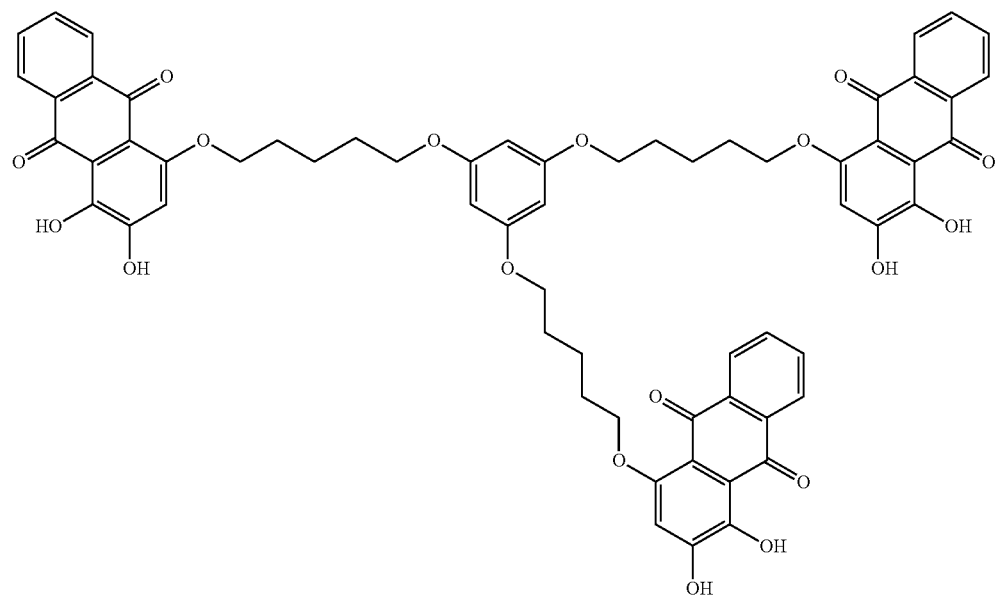
B-10
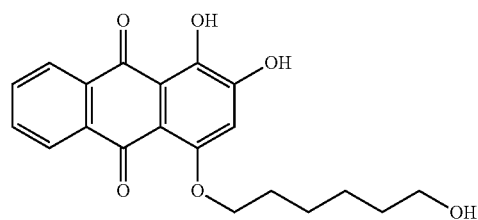
B-11
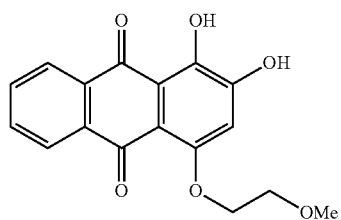
B-12

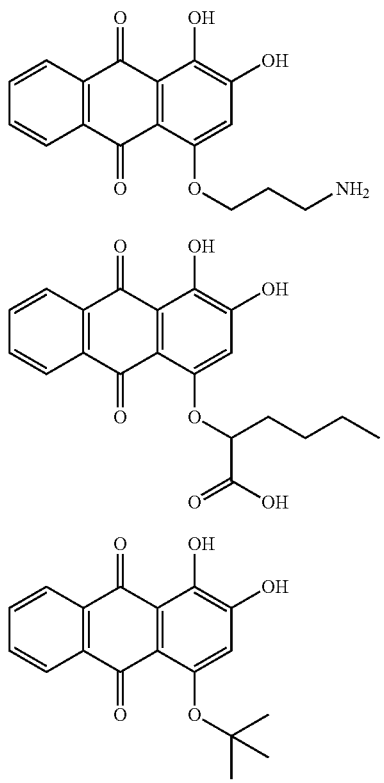

B-13

B-15

B-17

-continued

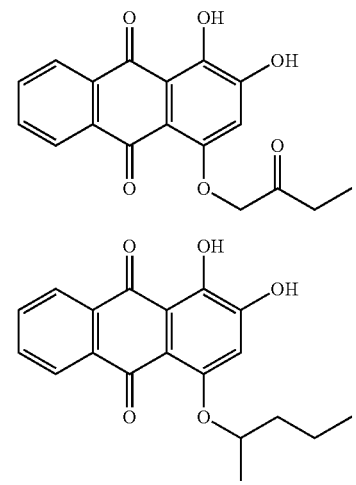

B-14

B-16

The alizarin derivative compound obtained by the preparation method of the present invention can be applied in a wide range of various fields, such as compounds, complexes, and Lake pigments that are used in organic electronics fields (for example, a colorant-sensitized solar cell, an organic thin film solar cell, an organic imaging element, an organic semiconductor, an organic EL element, an electrophotographic photoreceptor, and the like), color material fields (for example, an ink for an inkjet, color copies in a sublimation transfer mode, an ink dye, a color filter, silver halide photosensitive materials, printing, optical recording media, colorants for food, and the like), physiologically active materials (for example, an anticancer agent, a hair growth promoter, and the like), an electrolyte solution, and the like.

Particularly, a preferable embodiment regarding the application of the alizarin derivative compound obtained by the preparation method of the present invention from the viewpoint that the alizarin derivative compound acts as an n-type semiconductor is an embodiment in which the alizarin derivative compound is included in a photoelectric conversion film, an embodiment in which the alizarin derivative compound is included in a layer provided with a photoelectric conversion element, and an embodiment in which the alizarin derivative compound is included in an undercoat layer provided with an electrophotographic photoreceptor.

Furthermore, it is preferable to use a product obtained by modifying the surface of an inorganic compound solid material such as a metal oxide and the like by the alizarin derivative compound with the use of a surface modification method as described in detail below when the alizarin derivative compound is included in an undercoat layer provided with a photoelectric conversion film, a photoelectric conversion element, or an electrophotographic photoreceptor.

Hereinbelow, a preferable embodiment regarding the application of the alizarin derivative compound obtained by the preparation method of the present invention will be further described.

[Surface Modification Method]

The surface modification method of the present invention is a surface modification method for an inorganic compound solid material, in which the alizarin derivative compound is bonded to the surface of the inorganic compound solid material through an oxygen atom obtained by the removal of a hydrogen atom from at least one hydroxyl group contained in the alizarin derivative compound represented by Formula (5) or (6) above.

<Inorganic Compound Solid Materials>

The inorganic compound solid material used in the surface modification method of the present invention is not particularly limited as long as the surface can be modified by the above-described alizarin derivative compound, but preferable examples thereof include a metal (Au, Ag, Cu, Pt, Pd, Hg, Fe, and the like), semiconductor compound (GaAs, InP, Si, CdS, CdSe, ZnS, ZnSe, SnSe, $FeS_2$, PbS, InP, GaAs, $CuInS_2$, $CuInSe_2$, and the like), an oxide or oxide film ($TiSrO_3$, $TiO_2$, $Nb_2O_3$, $Al_2O_3$, AgO, CuO, $Ta_2O_5$, $Zr/Al_2O_3$, glass, mica, $SiO_2$, $SnO_2$, $WO_3$, $GeO_2$, $ZrO_2$, ZnO, $V_2O_5$, $KTaO_3$, indium tin oxide(ITO), and the like), stainless steel (SUS), lead zirconate titanate PZT), silicon nitride ($Si_3N_4$, $SiN_x$), and the like.

As the inorganic compound solid material used in the surface modification method of the present invention, a metal oxide is preferable from the viewpoint of forming strong multiple bonds with the alizarin derivative. As the metal oxide, an oxide or oxide film ($TiSrO_3$, $TiO_2$, $Nb_2O_3$, $Al_2O_3$, AgO, CuO, $Ta_2O_5$, $Zr/Al_2O_3$, glass, mica, $SiO_2$, $SnO_2$, $WO_3$, GeO$_2$, ZrO$_2$, ZnO, V$_2$O$_5$, KTaO$_3$, ITO, and the like), SUS, PZT, and the like are preferably used.

As the metal oxide, TiO$_2$, Al$_2$O$_3$, SiO$_2$, ZrO$_2$, and ZnO are more preferable, and TiO$_2$, SiO$_2$, and ZnO are most preferable.

Further, as the inorganic compound solid material, for example, one obtained by subjecting an outermost layer of a substrate including an inorganic compound to an ozone treatment to produce a hydroxy group on the substrate, or one obtained by forming an SAM (self-assembled monolayer) film of a hydroxy group-containing alkanethiol on a metal surface can also be used.

The form of the inorganic compound solid material is not particularly limited, but it is preferably a fine particle, and in the surface modification method of the present invention, a fine particle of a metal oxide is preferably used.

Herein, the fine particle refers to a particle having an average particle diameter from 1 nm to 1000 nm, preferably an average particle diameter from 5 nm to 500 nm, and more preferably an average particle diameter from 10 nm to 300 nm.

The fine particle has its outer layer surface-treated. As the surface treatment, for example, a surface treatment by applying hexamethyldisilazane (HMDS), octadecyltrichlorosilane (OTS), Oxide-NH$_2$, and the like, hydrogen-terminal silicon (Si—H), and the like, silicon halide (Si—X (X=Cl, Br, I, and the like)), hydrogen-terminal diamond (C—H), or the like on a silicon dioxide surface can be applied.

<Formation of Bond of Surface of Inorganic Compound Solid Material with Alizarin Derivative Compound>

In the surface modification method of the present invention, the alizarin derivative compound is bonded to the surface of the inorganic compound solid material through an oxygen atom obtained by the removal of a hydrogen atom from at least one hydroxyl group contained in the alizarin derivative compound represented by Formula (5) or (6) above. The bond is a covalent bond or a coordination bond.

(Method for Forming Bond)

In the surface modification method of the present invention, examples of the method for bonding the alizarin derivative compound with the surface of the inorganic compound solid material include a method for forming a bond by a vacuum process and a method for forming a bond by a solution process.

Formation of a bond by a vacuum process refers to formation of a monomolecular film by a vacuum process. Specific examples thereof include physical vapor growth methods such as a vacuum vapor deposition method, a sputtering method, an ion-plating method, a molecular beam epitaxy (MBE) method, and the like, or chemical vapor deposition (CVD) methods such as plasma polymerization and the like.

Further, formation of a bond by a solution process refers to a method using a solution in which an alizarin derivative compound is dissolved or dispersed in a solvent. As this method, specifically, commonly-used methods such as a cast method, a blade coating method, a wire bar coating method, a spray coating method, a dipping (immersion) coating method, a bead-coating method, an air knife-coating method, a curtain-coating method, an inkjet method, a spin coat method, a Langmuir-Blodgett (LB) method, and the like can be used.

In the surface modification method of the present invention, it is preferable to use a solution process, and it is particularly preferable to use a cast method, a spin coat method, a dipping (immersion) coating method, or an inkjet method.

~Conditions in Case of Using Solution Process~

The conditions in the case of forming a bond with the alizarin derivative compound on the surface of the inorganic compound solid material (preferably on the surface of the fine particle) using a solution process will be described.

First, a solution in which a material including the alizarin derivative compound is dissolved or dispersed in a suitable organic solvent, (for example, hydrocarbon-based solvents such as hexane, octane, decane, toluene, xylene, ethylbenzene, 1-methyl naphthalene, and the like; ketone-based solvents such as acetone, methyl ethyl ketone, methyl isobutyl ketone, cyclohexanone, and the like; halogenated hydrocarbon-based solvents such as dichloromethane, chloroform, tetrachloromethane, dichloroethane, trichloroethane, tetrachloroethane, chlorobenzene, dichlorobenzene, chlorotoluene, 1,2-dichlorobenzene, and the like; ester-based solvents such as ethyl acetate, butyl acetate, amyl acetate, and the like; alcohol-based solvents such as methanol, propanol, butanol, pentanol, hexanol, cyclohexanol, methyl cellosolve (ethylene glycol monomethyl ether), ethyl cellosolve (ethylene glycol monoethyl ether), ethylene glycol, and the like; ether-based solvents such as dibutyl ether, tetrahydrofuran, dioxane, anisole, and the like; and polar solvents such as N,N-dimethylformamide, N,N-dimethylacetamide, 1-methyl-2-pyrrolidone, 1-methyl-2-imidazolidinone, dimethylsulfoxide, and the like) and/or water is prepared.

Next, by providing the solution to the inorganic compound solid material by the above-described various methods, bringing the surface into contact with the solution, and then removing the solvent contained in the solution, a bond is formed via an oxygen atom between the surface and the alizarin derivative compound.

The concentration of the alizarin derivative compound in the solution is preferably 0.1% by mass to 80% by mass, and more preferably 0.1% by mass to 10% by mass.

The alizarin derivative compound obtained by the preparation method of the present invention is suitable for formation of a bond particularly by a solution process. The reason for this is that it is insufficient to merely dissolve a material in a solvent in order to apply the solution process in the surface modification method, and after providing the surface of the solid material with the solution in which the material has been dissolved in the solvent, crystallization does not occur in the process of forming a bond through evaporation of the solvent, and in this regard, the alizarin derivative compound used in the surface modification method of the present invention is superior in that such crystallization does not easily occur.

Furthermore, it is also possible to use a resin binder in the surface modification method of the present invention. In this case, the alizarin derivative compound and the resin binder are dissolved or dispersed in the above-described suitable solvent to give a solution, and the solution is brought into contact with the surface of the inorganic compound solid material by the above-described various methods, thereby forming a bond between the surface and the alizarin derivative compound.

Examples of the resin binder include insulating polymers such as polystyrene, polycarbonate, polyarylate, polyester, polyamide, polyimide, polyurethane, polysiloxane, polysulfone, polymethyl methacrylate, polymethyl acrylate, cellulose, polyethylene, polypropylene, PVA, and a modified product thereof (for example, polybutyral, and the like), and the like, and copolymers thereof, photoconductive polymers such as polyvinyl carbazole, polysilane, and the like, electrically conductive polymers such as polythiophene, polypyrrole, polyaniline, polyparaphenylenevinylene, and the like, and others.

The resin binders may be used alone or in combinations of two or more kinds thereof. From consideration of the mechanical strength of thin film, resin binders having high glass transition temperatures are preferable, and from consideration of the charge-transfer rate in the thin film, resin binders of a polar group-free structure, a photoconductive polymer, and an electrically conductive polymer are preferable.

In the case of using the resin binder, the amount used thereof is not particularly limited, but it is preferably used in an amount of 0.1% by mass to 30% by mass in the solid contents of a coating film including the alizarin derivative compound. Further, in the case in which the inorganic compound solid material that has been surface-modified by the surface modification method of the present invention is applied in the applications of organic semiconductors, it is more preferable not to use the resin binder.

Furthermore, when a bond between the alizarin derivative compound and the surface of the inorganic compound solid material is formed, the inorganic compound solid material in which the solution including the alizarin derivative compound is provided on the surface may be heated or cooled. The temperature for heating or cooling is not particularly limited, but it is preferably 0° C. to 200° C.

[Photoelectric Conversion Film, Photoelectric Conversion Element, and Electrophotographic Photoreceptor]

~Photoelectric Conversion Film and Photoelectric Conversion Element~

Examples of preferable embodiments regarding the application of the alizarin derivative compound obtained by the preparation method of the present invention include a photoelectric conversion film (the photoelectric conversion film of the present invention), a photoelectric conversion element (the photoelectric conversion element of the present invention), and an electrophotographic photoreceptor (the electrophotographic photoreceptor of the present invention).

The photoelectric conversion film or the photoelectric conversion element of the present invention can be applied to specifically, for example, photosensors (see, for example, JP-A Nos. 2003-234460, 2003-332551, 2005-268609, and 2008-63226 (used as a photosensitized solar cell)), organic thin film solar cells (see "Organic Photovoltaics" (2005 annul, Taylor & Francis) pp. 49-104, Chemical Reviews, 2007, vol. 107, pp. 1324-1338), and a photoelectric conversion film or photoelectric conversion element having the structure described in Journal of Photochemistry and Photobiology A: Chemistry, 2004, vol. 168, p. 191, JP-A No. 2008-276225, and the like.

The photoelectric conversion film and the photoelectric conversion element of the present invention have an easier preparation step, as compared with the case of using inorganic semiconductor materials such as silicon and the like. Further, particularly, in view of film formability by a wet process, it becomes possible to fabricate an element having a large area at a low temperature and at low cost.

In particular, as for the applications where the photoelectric conversion film and the photoelectric conversion element of the present invention are used, the photoelectric conversion film and the photoelectric conversion element can be useful in terms of use as a photoelectric conversion film and a photoelectric conversion element for a solid imaging element for a color filter. For example, instead of formation of the photoelectric conversion element as described in JP-A No. 2009-99866, in the case where the photoelectric conversion element of the present invention is applied, it is possible to provide a photoelectric conversion element having high durability at lower cost.

~Electrophotographic Photoreceptor~

The electrophotographic photoreceptor of the present invention has at least one of an undercoat layer and a photosensitive layer on a conductive base, in which the undercoat layer contains the alizarin derivative compound obtained by the preparation method of the present invention. The alizarin derivative compound is preferably bonded to the surface of an inorganic fine particle such as metal oxide and the like contained in the undercoat layer by the above-described surface modification method of the present invention.

Since the alizarin derivative compound obtained by the preparation method of the present invention has high solubility and no change in the bonding performances of inorganic fine particles such as metal oxide and the like, as compared with a case in which a conventional compound used in the same application embodiment as an application in an electrophotographic photoreceptor, a grain boundary is not generated in the interface of the inorganic fine particles and the homogeneity is high. As a result, from the electrophotographic photoreceptor of the present invention, good image quality without generation of a ghost, fogging, or black spots can be obtained. Further, excellent preservation property without generation of black spots due to leak defects is exhibited.

As the basic constructions of the conductive base, the undercoat layer, the photosensitive layer, and the like, which can each be applied in the electrophotographic photoreceptor of the present invention, for example, those described in each publication of JP-A Nos. 2006-30697, 2009-58788, 2009-122322, and 2009-69410 can be applied. This application claims priority from Japanese Patent Application Nos. 2009-277962 filed on Dec. 7, 2009, and 2010-64060 filed on Mar. 19, 2010, the disclosures of which are incorporated by reference herein.

EXAMPLES

Hereinbelow, the present invention will be described in detail with reference to Examples, but the present invention is not limited to these Examples.

Example 1

The compound (B-1) as described above as the alizarin derivative compound of the present invention was synthesized in the following manner.

1. Synthesis of Compound (A-1)

First, the compound (A-1) was synthesized by using purpurin as a starting raw material and carrying out a protection step (step (A)) and an alkylation step (step (B1)), as described in Synthesis Example (1) or Synthesis Example (2) as an alternative method, each shown below.

Furthermore, as the purpurin and the dichlorodiphenyl methane used in the following Synthesis Example, a commercially available product was used in Synthesis Method (1), and a product separately synthesized was used in Synthesis Method (2), but a product separately synthesized may be used in Synthesis Example (1) and a commercially available product may be used in Synthesis Method (2).

Synthesis Example (1) for Compound (A-1)

<Protection Step (Step (A))>

100 g of purpurin (manufactured by Tokyo Chemical Industry Co., Ltd.) was dissolved in 600 mL of N,N'-dimethylacetamide, followed by addition of 108 g of potassium carbonate, and then 111 g of α,α-dichlorodiphenyl methane (manufactured by Tokyo Chemical Industry Co., Ltd.) was added dropwise thereto. After performing a reaction at 80° C. for 9 hours, the reaction liquid was transferred to a mixed solvent of 1 L of water and 1 L of methanol. The solution was stirred in this state, cooled to room temperature, and then filtered. The obtained crude crystal was washed with 1 L of water and 1 L of methanol, and dried at 50° C. to obtain 136 g of a desired compound (1) (a compound having the structure shown below).

Further, the compound (1) can also be obtained by using an alternative method below as a protection step.

<Alternative Method for Protection Step (Step (A))>

To a solution obtained by dissolving 51.5 g of potassium hydroxide in 800 mL of water, and adding 200 g of purpurin (manufactured by Tokyo Chemical Industry Co., Ltd.) thereto were added 78.1 g of tetrabutylammonium bromide, 500 mL of toluene, and 117 g of potassium carbonate, followed by heating to 70° C. Thereafter, 200 g of diphenyl dichloromethane (manufactured by Tokyo Chemical Industry Co., Ltd.) was added dropwise thereto, followed by heating and refluxing for 5 hours, and the reaction liquid was transferred to 6 L of methanol. The precipitated crystal was filtered, and washed with 1 L of water and 1.5 L of methanol to obtain 300 g of a desired compound (1)(a compound having the structure shown below).

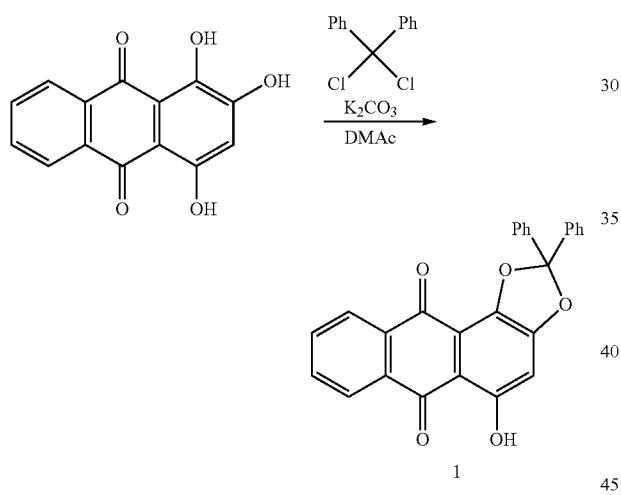

<Alkylation Step (Step (B1))>

4.4 g of a 50% aqueous potassium hydroxide solution, 11.6 g of tetrabutylammonium bromide, 15 mL of water, and 30 mL of toluene were added to 12.6 g of the obtained compound (1), and then 7.5 g of ethyl iodide was added dropwise thereto, followed by heating and refluxing at 65° C. for 6 hours. After leaving to be cooled to room temperature, the precipitated crystal was washed with water and then washed with methanol to obtain a crude crystal, which was subjected to a silica gel column chromatography treatment to obtain 8.9 g (purity 99.3%) of a desired compound (A-1) (a compound having the structure shown below).

Further, the compound (A-1) can also be obtained by using the alternative method below as an alkylation step.

<Alternative Method for Alkylation Step (Step (B1))>

6.2 g of potassium hydroxide, 16.0 g of tetrabutylammonium bromide, 50 mL of water, and 50 mL of toluene were added to 42.0 g of the obtained compound (1), and then the reaction liquid was heated to 55° C. Then, 10 mL of ethyl iodide was added dropwise thereto, followed by heating for 2.5 hours. Thereafter, 2.5 mL of ethyl iodide and 1.5 g of potassium hydroxide were further added thereto, followed by heating for an additional 2 hours. The reaction liquid was transferred in this state to 0.6 L of methanol, followed by stirring. After cooling to room temperature, the precipitated crystal was filtered and washed with 0.2 L of water and 0.3 L of methanol to obtain 36.6 g of a crude crystal A. 30 g of the obtained crude crystal A was dissolved in 300 mL of tetrahydrofuran by heating, and filtered through Celite at room temperature. 450 mL of water was added to the filtrate and the precipitated crystal was filtered to obtain 27.7 g of a crude crystal B. 25 g of the obtained crude crystal B was put into 75 mL of N,N'-dimethylacetamide, followed by heating to 100° C. and then cooling to room temperature, and the precipitated crystal was filtered to obtain 17.8 g (purity 96.3%) of a compound (A-1) (a compound having the structure shown below).

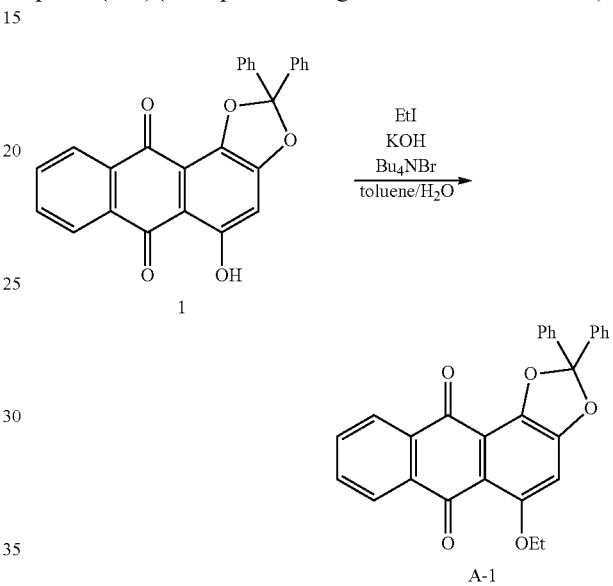

Synthesis Example (2) for Compound (A-1)

Purpurin and dichlorodiphenyl methane were synthesized by the method described in the following documents.
(1) Purpurin: "Review on Synthetic Dyes" (Sankyo Publishing), Horiguti Hiroshi, p. 541
(2) Dichlorodiphenyl methane: "J. Med. Chem., 2008, 51, 2115"

Details on these are as follows.

~Synthesis of Purpurin~

A suspension of 17.5 g of manganese dioxide/40 g of concentrated sulfuric acid, that had been prepared by putting 9.0 g of water and 130 g of 96% sulfuric acid into 30 g of alizarin (manufactured by Sigma-Aldrich Corporation), followed by ice-cooling, was added over 1 hour to a reaction liquid while maintaining it at 10° C. or lower. After 2 hours, the reaction liquid was poured into 1 L of water, with the inside of the container being washed with 400 mL of water, and filtered. The crystal collected by filtration was washed with 300 mL of methanol and dried to obtain 32.4 g of purpurin.

~Synthesis of Dichlorodiphenyl Methane~

25.6 mL of N,N-dimethylformamide (DMF) (manufactured by Wako Pure Chemical Industries Ltd.) was added to 60.1 g of benzophenone (manufactured by Wako Pure Chemical Industries Ltd., and then 60.2 mL of thionyl chloride (manufactured by Wako Pure Chemical Industries Ltd.) was added dropwise thereto, followed by performing a reaction at a reaction temperature of 75° C. for 12 hours. After confirming the production of the dichlorodiphenyl methane by means of 1H-NMR, 60 mL of toluene and 80 mL of water were added thereto under ice-cooling to perform liquid separation and remove the aqueous layer, thereby obtaining a dichlorodiphenyl methane/toluene solution.

<Protection Step (Step (A))>

6.18 g of potassium hydroxide, 20.8 g of potassium carbonate, 140 mL of water, and 16.1 g of tetrabutylammonium bromide were added to 25.6 g of the obtained purpurin, followed by heating at 80° C., and the above-described dichlorodiphenyl methane/toluene solution was added dropwise thereto.

<Alkylation Step (Step (B1))>

Three hours later, after confirming the proceeding of the introduction of a protecting group, the reaction temperature was lowered to 60° C., and 18.5 g of sodium hydroxide and 23.4 g of iodoethane were added thereto. The reaction liquid was poured into a mixed solvent of 300 mL of methanol and 300 mL of ethyl acetate to precipitate a crystal.

Thereafter, the crystal was filtered, washed with 100 mL of methanol and 100 mL of water, and further washed with 100 mL of methanol to obtain 38.2 g of a crude crystal A. 15.0 g of the obtained crude crystal A was dissolved in 150 mL of tetrahydrofuran by heating, followed by filtration through Celite at room temperature. 200 mL of water was added to the filtrate, and the precipitated crystal was filtered to obtain 9.3 g (purity 97.4%) of the compound (A-1).

2. Synthesis of Compound (B-1)

Next, by subjecting the obtained compound (A-1) to the deprotection step (Step (B2)) shown below, a compound (B-1) which was a desired product was obtained.

<Deprotection Step (Step (B2))>

150 g of the obtained compound (A-1) was added to and dissolved in 150 g of sulfuric acid, followed by heating at 60° C. for 1 hour. The reaction liquid was slowly transferred to 1.5 L of methanol that had been ice-cooled to 0° C., and the obtained crystal was filtered, and washed with 1 L of water and 1 L of methanol to obtain 93 g (purity 97.9%) of a desired compound (B-1).

Further, the compound (B-1) can also be obtained by using an alternative method below as a deprotection step.

<Deprotection Step (Alternative Method for Step (B2))>

4.5 g of the obtained compound (A-1) was dissolved in 45 mL of toluene and 35 mL of methylene chloride, followed by ice-cooling to 0° C., and then 3 mL of concentrated sulfuric acid was added dropwise thereto. The solution was maintained at 0° C. for 1 hour, and then left to become room temperature. After separating the supernatant and the oily residue at the bottom of the flask, the supernatant was removed by decantation, and water was added to the oily residue, followed by filtration, thereby obtaining a red powder. In addition, the powder was dispersed in methanol, followed by stirring for a while and then filtering, thereby obtaining 2.75 g (purity 99.4%) of a desired compound (B-1).

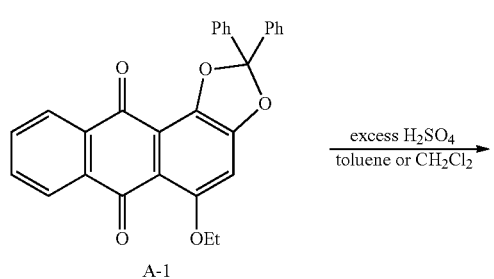

A-1

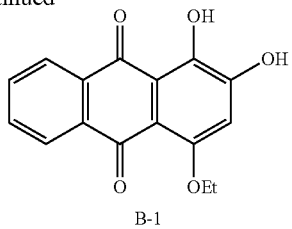

B-1

The obtained compound (B-1) was subjected to 1H-NMR measurement. The results are shown below.

1HNMR (300 MHz, CDCl3) δ 13.39 (s, 1H), 8.32 (d, 1H), 8.26 (d, 1H), 7.81 (dd, 1H), 7.73 (dd, 1H), 6.98 (s, 1H), 6.45 (1s, br), 4.21 (q, 2H), 1.58 (t, 3H).

Example 2

<Alkylation Step (Step (B1))>

4.04 g of a 50% aqueous potassium hydroxide solution, 11.6 g of tetrabutylammonium bromide, 25 mL of water, and 40 mL of toluene were added to 12.6 g of the compound (1) obtained in a manner substantially similar to Example 1, and then 5.61 g of iodobutane was added dropwise thereto, followed by heating and refluxing at 100° C. for 7 hours. After leaving to be cooled to room temperature, toluene was evaporated and the precipitated crystal was washed with water and then washed with methanol to obtain a crude crystal. The crystal was subjected to a silica gel column chromatography treatment to obtain 8.5 g of a desired compound (A-2) (a compound having the structure shown below).

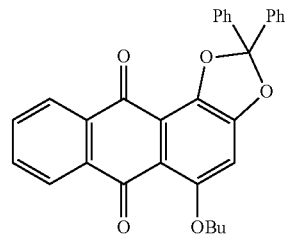

A-2

<Deprotection Step (Step (B2))>

7.5 g of the obtained compound (A-2) was dissolved in 70 mL of toluene and 30 mL of methylene chloride, followed by ice-cooling to 0° C., and then 5 mL of concentrated sulfuric acid was added dropwise thereto. The solution was maintained at 0° C. for 1 hour and then left to become room temperature. After separating the supernatant and the oily residue at the bottom of the flask, the supernatant was removed by decantation, and water was added to the oily residue, followed by filtration, thereby obtaining a red powder. In addition, the powder was dispersed in methanol, followed by stirring for a while and then filtering, thereby obtaining 5.00 g (purity 99.5%) of a desired compound (B-2).

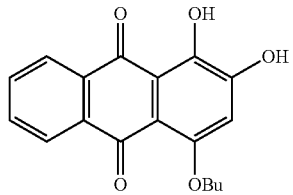

B-2

The obtained compound (B-2) was subjected to 1H-NMR measurement. The results are shown below.

1HNMR (300 MHz, CDC13) δ 13.41 (s, 1H), 8.32 (d, 1H), 8.25 (d, 1H), 7.80 (dd, 1H), 7.72 (dd, 1H), 6.97 (s, 1H), 6.48 (1s, br), 4. 13 (t, 2H), 1.93 (m, 2H), 1.62 (m, 2H), 1.02 (t, 3H).

Example 3

<Alkylation Step (Step (B1))>

127.6 g of silver oxide and 500 mL of toluene were added to 115.7 g of the compound (1) obtained in a same manner substantially similar to Example 1, and then 92.7 g of iodooctane was added dropwise thereto, followed by heating and refluxing for 7 hours. In addition, 47 g of silver oxide and 86 g of iodooctane were further added thereto, followed by heating and refluxing for 3 hours. After leaving to be cooled to room temperature, silver oxide was filtered off and toluene was evaporated with an evaporator, and the residue was purified by silica gel column chromatography to obtain 100 g of a concentrated liquid including a compound (A-3) having the structure shown below, which was a desired product.

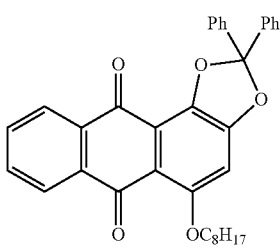

A-3

<Deprotection Step (Step (B2))>

100 g of concentrated sulfuric acid was added to the concentrated liquid including the obtained compound (A-3), followed by heating at 70° C. for 2 hours. The reaction liquid was slowly transferred to 0.5 L of methanol and the precipitated crystal was filtered to obtain 66 g (purity 95.6%) of a compound (B-3) below.

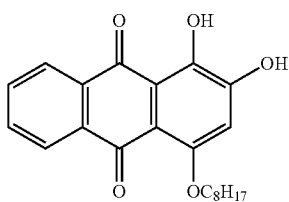

B-3

The obtained compound (B-3) was subjected to 1H-NMR measurement. The results are shown below.

1HNMR (300 MHz, CDC13) δ 13.41 (s, 1H), 8.32 (d, 1H), 8.26 (d, 1H), 7.80 (dd, 1H), 7.72 (dd, 1H), 6.98 (s, 1H), 6.45 (1s, br), 4. 12 (t, 2H), 1.94 (m, 2H), 1.53 (m, 2H), 1.42~1.30 (m, 10H), 0.88 (t, 3H).

Example 4

<Alkylation Step (Step (B1))>

1.60 g of a 50% aqueous potassium hydroxide solution, 4.58 g of tetrabutylammonium bromide, 10 mL of water, and 25 mL of toluene were added to 5.97 g of the compound (1) obtained in a same manner substantially similar to that in Example 1, and then 2.20 g of 1,4-diiodobutane was added dropwise thereto, followed by heating and refluxing at 100° C. for 15 hours. After leaving to be cooled to room temperature, toluene was evaporated, and the precipitated crystal was filtered, and washed with water and then washed with toluene and methanol to obtain a crude crystal. Then, after filtration over Celite with chloroform, the concentrated liquid was subjected to a silica gel column chromatography treatment to obtain 2.82 g of a desired compound (A-4) (a compound having the structure shown below).

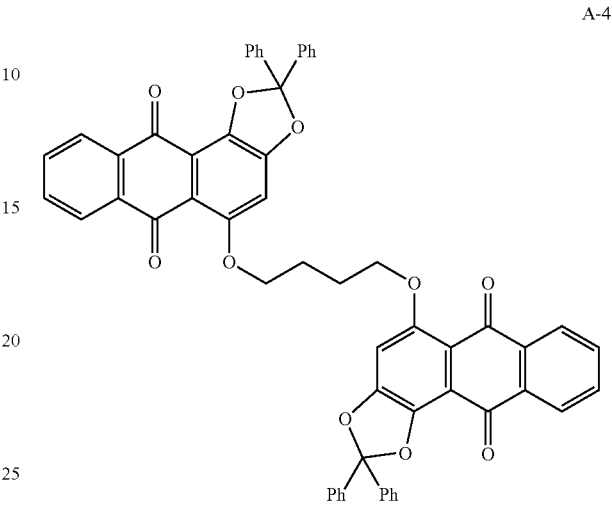

A-4

<Deprotection Step (Step (B2))>

2.80 g of the obtained compound (A-4) was dissolved in 50 mL of methylene chloride and ice-cooled to 0° C., and then 2 mL of concentrated sulfuric acid was added dropwise thereto. The solution was maintained at 0° C. for 1 hour and then left to become room temperature. After separating the supernatant and the oily residue at the bottom of the flask, the supernatant was removed by decantation, and methanol was added to the oily residue, followed by filtration, thereby obtaining a red powder. In addition, the powder was dispersed in methanol, followed by stirring for a while and then filtering, thereby obtaining 1.60 g of a desired compound (B-4).

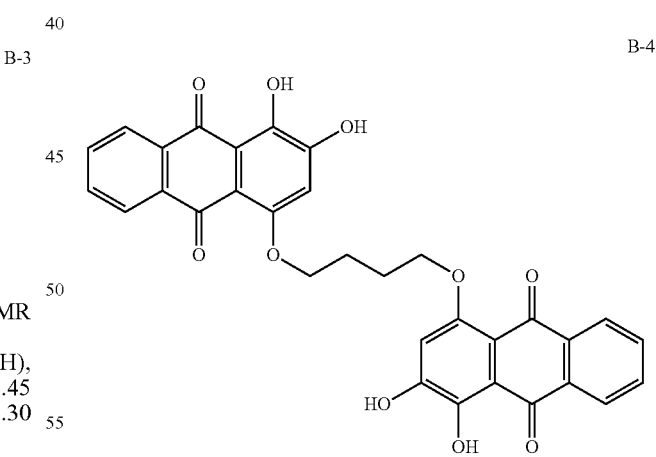

B-4

The analysis results of MALDI-MS (Matrix Assisted Laser Desorption/Ionization Mass Spectrometry) conducted on the obtained compound (B-4) are as follows.

MALDI-MS [M$^+$]+[Na$^+$=23]=589

Example 5

<Alkylation Step (Step (B1))>

3.64 g of a 50% aqueous potassium hydroxide solution, 9.67 g of tetrabutylammonium bromide, 30 mL of water, and 30 mL of toluene were added to 12.6 g of the compound (1) obtained in a same manner substantially similar to that in Example 1, and then 5.06 g of 1,6-diiodoheptane was added dropwise thereto, followed by heating and refluxing at 100° C. for 16 hours. After leaving to be cooled to room temperature, toluene was evaporated, and the precipitated crystal was filtered, and washed with water and then washed with ice-cooled methanol to obtain a crude crystal. Then, the crystal was subjected to a silica gel column chromatography treatment with methylene chloride, and washed with methanol to obtain 2.82 g of a desired compound (A-5) (a compound having the structure shown below).

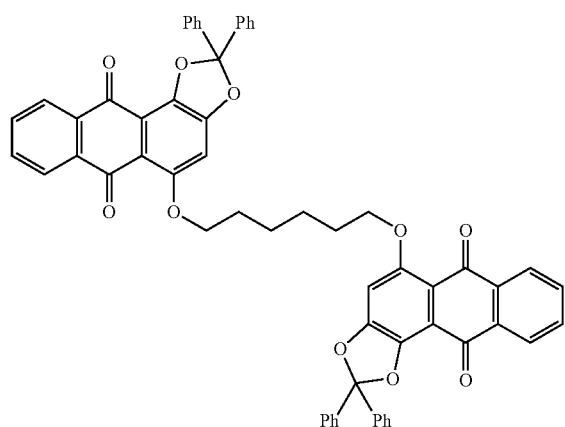

A-5

<Deprotection Step (Step (B2))>

5.62 g of the obtained compound (A-5) was dissolved in 100 mL of methylene chloride and ice-cooled to 0° C., and then 5 mL of concentrated sulfuric acid was added dropwise thereto. The solution was maintained at 0° C. for 1 hour and then left to become room temperature. After separating the supernatant and the oily residue at the bottom of the flask, the supernatant was removed by decantation, and methanol was added to the oily residue, followed by filtration, thereby obtaining a red powder. In addition, the powder was dispersed in 100 mL of dimethyl sulfoxide. The dispersion was heated to 140° C., stirred for 30 minutes, then cooled to room temperature, filtered, and washed with methanol to obtain 1.50 g (purity 95.0%) of a desired compound (B-5).

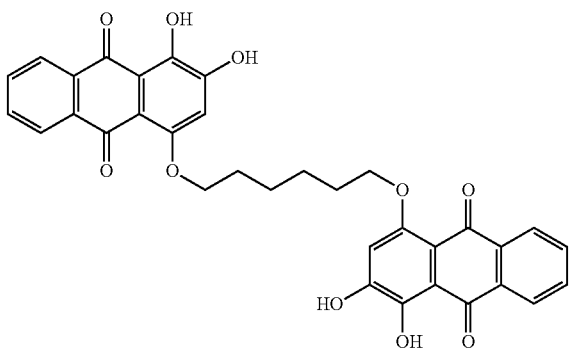

B-5

The obtained compound (B-5) was subjected to 1H-NMR measurement. The results are shown below.

1HNMR (300 MHz, DMSO) δ 13.14 (s, 2H), 10.84 (s, 2H), 8.10 (d, 2H), 7.99 (d, 2H), 7.80 (m, 4H), 6.91 (s, 2H), 4.08 (t, 4H), 1.82 (m, 4H), 1.69 (m, 4H).

Example 6

<Alkylation Step (Step (B1))>

3.64 g of a 50% aqueous potassium hydroxide solution, 9.67 g of tetrabutylammonium bromide, 30 mL of water, and 30 mL of toluene were added to 12.6 g of the compound (1) obtained in a same manner substantially similar to that in Example 1, and then 5.48 g of 1,8-diiodooctane was added dropwise thereto, followed by heating and refluxing at 100° C. for 16 hours. After leaving to be cooled to room temperature, toluene was evaporated, and the precipitated crystal was filtered, and washed with water and then washed with ice-cooled methanol to obtain a crude crystal. Then, the crystal was subjected to a silica gel column chromatography treatment with methylene chloride, and washed with methanol to obtain 4.18 g of a desired compound (A-6) (a compound having the structure shown below).

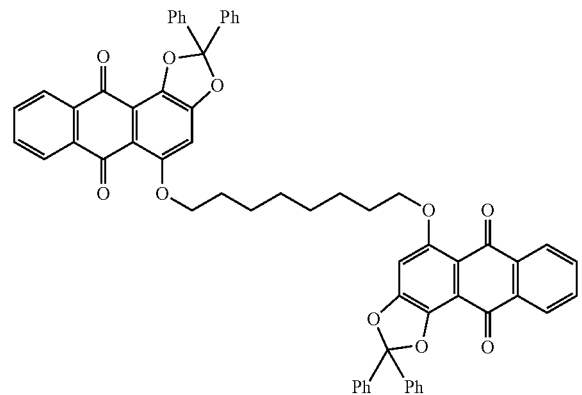

A-6

<Deprotection Step (Step (B2))>

4.18 g of the obtained compound (A-6) was dissolved in 100 mL of methylene chloride and ice-cooled to 0° C., and then 4 mL of concentrated sulfuric acid was added dropwise thereto. The solution was maintained at 0° C. for 1 hour and then left to become room temperature. After separating the supernatant and the oily residue at the bottom of the flask, the supernatant was removed by decantation, and methanol was added to the oily residue, followed by filtration, thereby obtaining a red powder. In addition, the powder was dispersed in 100 mL of dimethyl sulfoxide. The dispersion was heated to 140° C., stirred for 30 minutes, then cooled to room temperature, filtered, and washed with methanol to obtain 2.00 g (purity 96.0%) of a desired compound (B-6).

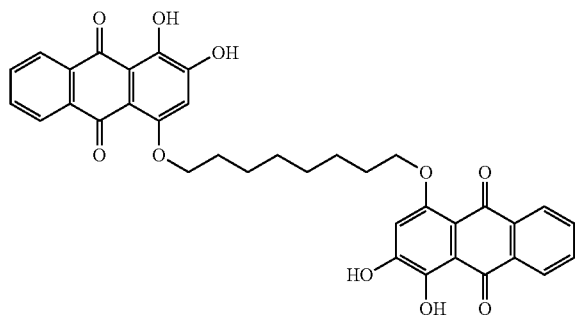

B-6

The obtained compound (B-6) was subjected to 1H-NMR measurement. The results are shown below.

1HNMR (300 MHz, DMSO) δ 13.24 (s, 2H), 10.97 (s, 2H), 8.11 (dd, 4H), 7.83 (m, 4H), 4.04 (t, 4H), 1.78 (m, 4H), 1.57 (m, 4H), 1.42 (m, 4H).

Example 7

<Alkylation Step (Step (B1))>

According to the method described in the document (J. Org. Chem., 2002, vol. 17, p. 6282), a mixture having the compound (2) with the following structure as a main component was obtained.

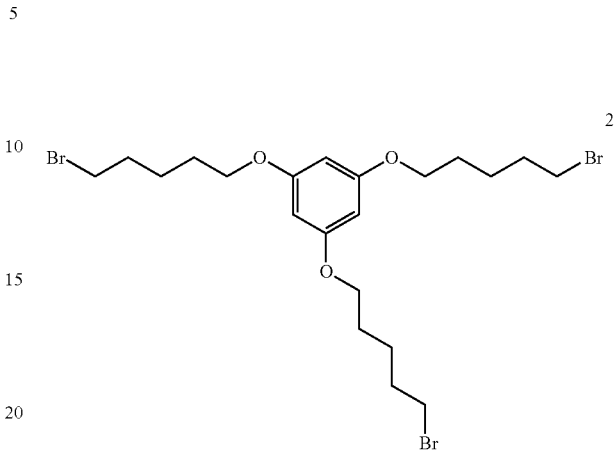

2

10 mL of toluene and 30 g of silver oxide were added to a mixture of 1.0 g of a mixture including the obtained compound (2) and 2.2 g of the compound (1) obtained in a same manner substantially similar to that in Example 1, followed by heating and refluxing for 20 hours. The residue was filtered through Celite with methylene chloride and then concentrated, followed by purification by silica gel column chromatography, thereby obtaining 0.1 g of a desired compound (A-10).

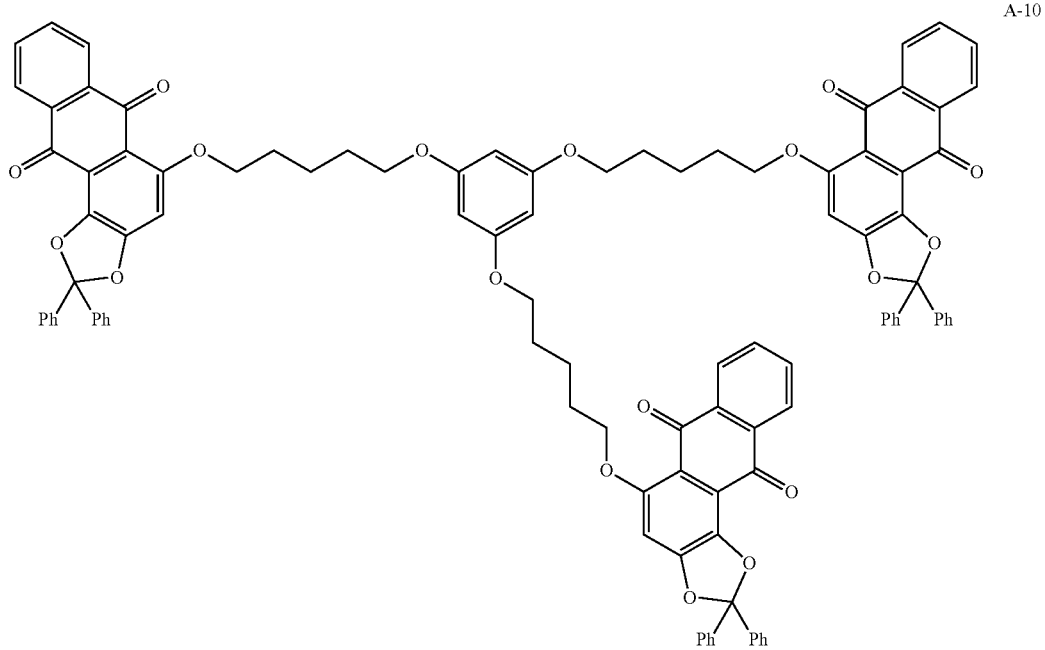 [SMILES: O=C1c2ccccc2C(=O)c2c3c(cc(OCCCCCOc4cc(OCCCCCOc5cc6c(c7c5C(=O)c5ccccc5C7=O)OC(c5ccccc5)(c5ccccc5)O6)cc(OCCCCCOc5cc6c(c7c5C(=O)c5ccccc5C7=O)OC(c5ccccc5)(c5ccccc5)O6)c4)c21)OC(c1ccccc1)(c1ccccc1)O3]

A-10

<Deprotection Step (Step (B2))>

0.1 g of the obtained compound (A-10) was dissolved in 0.1 mL of concentrated sulfuric acid, followed by heating at 60° C. for 1 hour. Thereafter, the solution was cooled to room temperature, 10 mL of methanol was added thereto, and the obtained crystal was filtered.

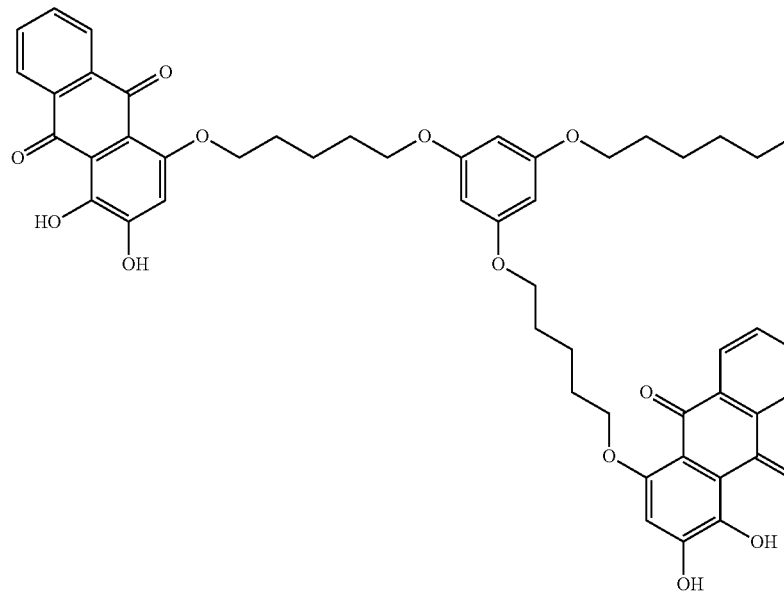

B-10

The analysis results of MALDI-MS conducted on the obtained compound (B-10) are as follows.

MALDI-MS [M$^+$]+[Na$^+$=23]=1121

Comparative Example 1

By the synthesis method shown below, the compound (C-1) shown below was obtained.

5.12 g of purpurin (manufactured by Tokyo Chemical Industry Co., Ltd.) was dissolved in 30 mL of N,N'-dimethylformamide, followed by addition of 2.76 g of potassium carbonate, and 4.80 g of iodooctane was added dropwise thereto. After performing a reaction at 70° C. for 7 hours and then ice-cooling to an inner temperature of 0° C., 20 mL of diluted hydrochloric acid (2 mL concentrated hydrochloric acid diluted with 18 mL of water) was used for neutralization, and then 30 mL of water was added thereto to obtain a crude crystal. The obtained crude crystal was purified by silica gel chromatography with ethyl acetate to obtain 0.75 g of a desired compound (C-1).

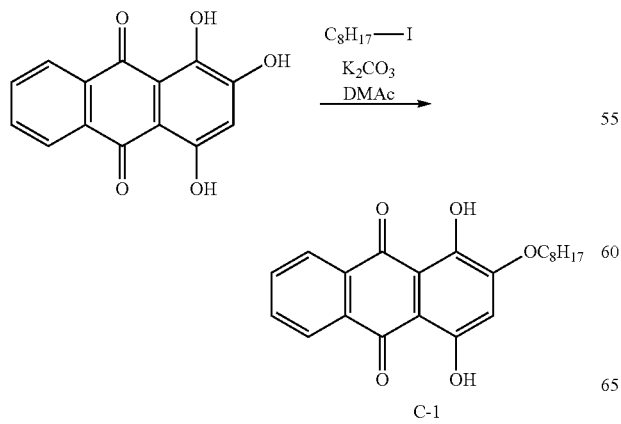

C-1

The obtained compound (C-1) was subjected to 1H-NMR measurement. The results are shown below.

1HNMR (300 MHz, CDC13) δ 13.58 (s, 1H), 13.49 (s, 1H), 8.45 (dd, 2H), 7.80 (dd, 4H), 6.68 (s, 1H), 4.15 (t, 2H), 1.92 (m, 2H), 1.72~1.25 (m, 10H), 0.88 (t, 3H).

Comparative Example 2

The compound 4 (which is referred to the compound (C-2) in the present specification) described in the above-described Synthesis, 1991, p. 438 was obtained by the method described in the same document.

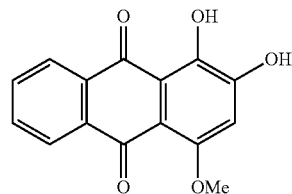

C-2

Comparative Example 3

The compound 14 (which is referred to the compound (C-3) in the present specification) described in the above-described Aus. J. Chem., 1976, vol. 29, p. 2231 was obtained by the method described in the same document.

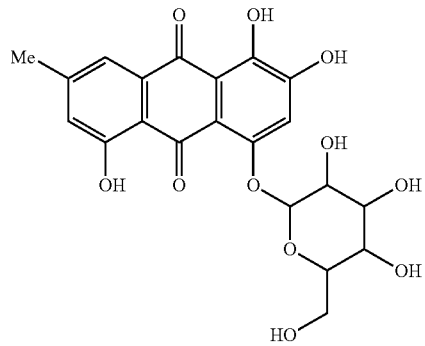

C-3

Comparative Example 4

<Protection Step>

The compound (1) was obtained in a same manner substantially similar to the protection step in Example 1.

<Alkylation Step>

1.68 g of methane iodide, 1.85 g of silver oxide, and 10 mL of toluene were added to 0.4 g of the obtained compound (1), followed by heating and refluxing at 70° C. for 2 hours. After leaving to be cooled to room temperature, silver oxide was filtered off and toluene was evaporated with an evaporator to obtain 0.40 g of a crystal of a compound (A-7) having the following structure, which was a desired product.

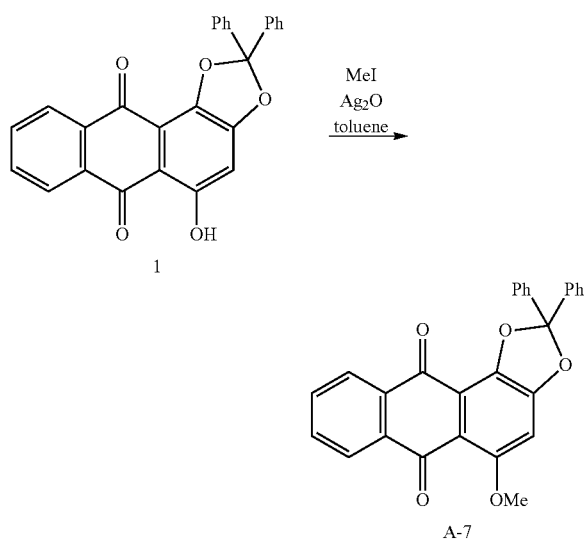

<Deprotection Step>

20 mL of toluene was added to 0.4 g of the obtained compound (A-7), and then 2 mL of 35% aqueous hydrochloric acid was added thereto, followed by heating and refluxing for 1 hour. After leaving to be cooled to room temperature, toluene was evaporated with an evaporator to obtain only 0.20 g of purpurin, but not the compound (C-2) (having the structure above) as a desired product.

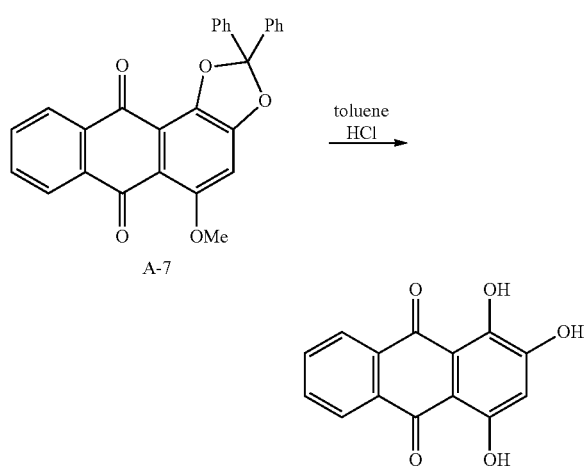

This confirms that the compound C-2 (purpurin substituted with methyl at the 4-position) is not stable in the presence of acids and is easily deprotected.

[Evaluation 1]

Each of known compounds such as alizarin, purpurin, quinizarin, chrysazin, and anthrarufin, and the compounds (B-1) to (B-6), and (B-10) obtained in Examples 1 to 7, and the compounds (C-1) to (C-3) obtained in Comparative Example 1 to 3 were subjected to the measurements shown below.

<Measurement 1: Measurement of Adsorption Rate to Zinc Oxide and Maximum Value in Absorption Spectrum>

An adsorption rate to zinc oxide and a maximum value in the absorption spectrum of each compound were measured by the measurement method shown below.

~Measurement Method~

5 mL of methyl ethyl ketone (MEK) was added to $1 \times 10^{-5}$ moles of an organic material to be tested placed in a transparent screw-cap bottle (15 ml) to prepare a solution of the organic material to be tested. 300 mg of zinc oxide (particle diameter 70 nm) was weighed and the solution of the organic material to be tested was added thereto. Thereafter, after stirring at room temperature for 3 hours, zinc oxide particles were left to be naturally settled overnight. 2 mL of the supernatant was collected in a glass syringe and filtered through a cartridge-type filter (non-aqueous, 0.45 μm or 0.2 μm). 0.5 mL of the filtrate was measured using a hole pipette and diluted by the addition of 20 mL of MEK to a measuring flask, and an absorption spectrum in the range from 350 nm to 800 nm was measured using a UV-3100PC; trade name, manufactured by Shimadzu Corporation. The rate of decrease in the absorbance at the absorption maximum was defined as an adsorption rate.

<Measurement 2: Measurement of Maximum Value in Reflection Spectrum of Adsorbed Zinc Oxide>

For each compound, a maximum value in the reflection spectrum of the adsorbed zinc oxide was measured by the measurement method shown below.

~Measurement Method~

For each of the solutions of the organic material to be tested that had been stirred and had zinc oxide particles left to be naturally settled in Measurement 1, after the stirrer was removed, precipitates were gathered using an OMNIPORE (trade name) membrane filter having a diameter of 0.45 μm or 0.1 μm/25 mm. The precipitates and the remaining supernatants were all washed with acetone and put into a filter. The resultant was gently aspirated and acetone was allowed to flow therethrough until the waste liquid became clear. After discharging acetone and drying, adsorbed powders were collected from the filter. The adsorbed powders obtained were spread on the adhesive side of a MYLAR (trade name) tape, and a glass slide cut to ½ at around 20-mm square was adhered thereto. In addition, it was fixed with a MYLAR (trade name) tape and the excessive tape was cut off. For diffuse reflectance measurements, measurement was conducted in the range from 300 nm to 800 nm using a UV-3100PC ;tarde name, manufactured by Shimadzu Corporation.

The above results are shown in Table 1.

TABLE 1

| Compound | Purity (%) | Adsoption Rate (%) | Absorption Spectrum λmax (nm) | Reflection Spectrum λmax (nm) |
|---|---|---|---|---|
| Alizarin | 93.6 | 73 | 426 | 526 |
| Purpurin | 83.1 | 86 | 482 | 525 |
| Quinizarin | 99.3 | 17 | 480 | 519, 575 |
| Chrysazin | 98.8 | 12 | 429 | 510 |
| Anthrarufin | 90.5 | 32 | 432 | 531 |
| Compound C-1 | 94.0 | 38 | 482 | 525, 558 |

TABLE 1-continued

| Compound | Purity (%) | Adsorption Rate (%) | Absorption Spectrum λmax (nm) | Reflection Spectrum λmax (nm) |
|---|---|---|---|---|
| Compound C-2 | 97.0 | 76 | 471 | 538 |
| Compound C-3 | — | 50 | 469 | 530 |
| Compound B-1 | 98.2 | 69 | 471 | 538 |
| Compound B-2 | 99.5 | 72 | 471 | 541 |
| Compound B-3 | 99.4 | 75 | 469 | 537 |
| Compound B-4 | — | 99 | 499 | 537 |
| Compound B-5 | 95.0 | 98 | 478 | 555 |
| Compound B-6 | 96.0 | 99 | 483 | 537 |
| Compound B-10 | — | 99 | 478 | 538 |

Example 8

The photoelectric conversion elements in Examples were prepared in the following manner.

A 25-mm square glass substrate equipped with an ITO electrode was subjected to ultrasonic cleaning with acetone, SEMICO CLEAN (trade name, manufactured by Furuuchi Chemical Corporation), and isopropyl alcohol (IPA), each for 15 minutes. After finally washing with boiling IPA, cleaning by $UV/O_3$ washing (cleaning by UV irradiation and/or ozone) was carried out. The substrate was then transferred into an organic vapor deposition chamber, and the pressure inside the chamber was reduced to a level of $1 \times 10^{-4}$ Pa or less. Subsequently, while rotating the substrate holder, m-MTDATA (4,4',4''-tris[3-methylphenyl(phenyl)-amino]triphenylamine) was vapor-deposited on the ITO electrode as a first charge-blocking layer at a vapor deposition rate of 0.05 nm/sec to 0.1 nm/sec to a thickness of 100 nm according to the resistance-heating method. Next, co-vapor deposition was conducted while keeping the vapor deposition rate of a p-type organic semiconductor of silicon 2,3-naphthalocyanine bis (trihexylsilyloxide) (purchased from Sigma-Aldrich Japan K. K. and purified by sublimation) at 0.3 nm/sec and also keeping the vapor deposition rate of an n-type organic semiconductor of fullerene C60 (purchased from Sigma-Aldrich Japan K. K. and purified by sublimation) at 0.3 nm/sec, and further while keeping the volume ratio of the p-type organic semiconductor to fullerene C60 at 1:1, thereby forming a photoelectric conversion layer in which the p-type semiconductor and fullerene C60 were mixed with each other with a total thickness of 10 nm. Further, co-vapor deposition was conducted while keeping the vapor deposition rate of silicon 2,3-naphthalocyanine bis(trihexylsilyloxide) (the same as described above) at 0.3 nm/sec to a total thickness of 20 nm, thereby forming a photoelectric conversion layer only for the p-type organic semiconductor. The total thickness of the photoelectric conversion layer was 30 nm.

Subsequently, a second charge-blocking layer was formed by a method in which a solution having 100 parts by mass of ZnO fine particles (average particle diameter 70 nm), 3 parts by mass of the compound (B-1) which was the alizarin derivative compound of the present invention, 30 parts by mass of polymethyl methacrylate (PMMA) (weight average molecular weight 50,000) as a binder, and 70 parts by mass of MEK dissolved therein was applied and then heated to 150° C., and then the solvent was removed.

Next, this substrate was transferred to a metal vapor deposition chamber while keeping it under vacuum. Aluminum was vapor-deposited on the second charge-blocking layer as a counter electrode to a thickness of 100 nm while keeping the pressure within the chamber at $1 \times 10^{-4}$ Pa or less. Also, the area of the photoelectric conversion region formed by the lowermost ITO electrode and the aluminum counter electrode was adjusted to 2 mm×2 mm. This substrate was transferred to a globe box wherein the concentrations of moisture and oxygen were kept at 1 ppm or less, respectively, without exposing to the atmosphere, and its sealing with glass to which a moisture absorbent had been applied was carried out using a UV-curable resin.

For the photoelectric conversion element thus prepared, a value of dark current flow at the time of no light irradiation and a value of a light current flowing at the time of light irradiation in the case in which an external electric field of $1.0 \times 10^6$ V/cm$^2$ (field strength: $1.0 \times 10^6$ V/cm$^2$) was applied to this element were measured using an energy quantum efficiency measuring apparatus manufactured by Optel (Cathley 6430: trade name, being used as the source meter), and the external quantum efficiency of the element was calculated therefrom. Light irradiation was carried out to the area of 1.5 mmφ of the 2 mm×2 mm photoelectric conversion region. The amount of irradiated light was adjusted to 50 μW/cm$^2$. Also, the value obtained by dividing the external quantum efficiency obtained at the time of light irradiation by the dark current density obtained at the time of no light irradiation was taken as an S/N ratio.

Furthermore, the present Example relates to a photoelectric conversion element in which a photoelectric conversion region having the same layer constitution as in (Example 1) of JP-A No. 2009-99866 except that the second charge-blocking layer (application layer) as described above is formed, instead of the Alq$_3$ layer formed as the second charge-blocking layer (vapor deposition layer), in the photoelectric conversion region formed in (Example 1) described in the above publication (Example 1), is formed. This photoelectric conversion element can be used as a photoelectric conversion element for a solid imaging element.

Comparative Examples 5 to 7

The photoelectric conversion elements in Comparative Examples 5 to 7 were prepared in substantially the same manner as that in Example 8 except that the compounds (C-1), (C-2) and (C-3) were individually used in Comparative Examples 5 to 7 as a comparative compound instead of the compound (B-1) used for formation of the second charge-blocking layer in Example 8.

The S/N ratios calculated for the photoelectric conversion elements prepared in Example 8 and Comparative Examples 5 to 7 are shown in Table 2, together with the adsorption rates (values obtained by Measurement 1 above) for the ZnO particles of the compounds (B-1), (C-1), (C-2), and (C-3) used in the second charge-blocking layer.

TABLE 2

| | Compound used in Second Charge-blocking Layer | Adsorption Rate to ZnO particles | S/N ratio |
|---|---|---|---|
| Example 8 | Compound B-1 | 69% | 450,000 |
| Comparative Example 5 | Compound C-1 | 38% | 40,000 |
| Comparative Example 6 | Compound C-2 | 76% | 60,000 |
| Comparative Example 7 | Compound C-3 | 50% | 30,000 |

From the results shown in Table 2, it can be seen that the photoelectric conversion element using the alizarin derivative compound of the present invention exhibits good electric characteristics (high S/N ratios) with the dark current being inhibited, as compared with the photoelectric conversion element in each of Comparative Examples in which the comparative compounds are used.

In particular, it was confirmed that although the photoelectric conversion element in Comparative Example 6 employs the compound (C-2) having substantially the same structure to that of the compound (B-1) except that methyl is substituted at the 4-position, it exhibits a low S/N ratio due to generation of a dark current. It is assumed that this is due to generation of traps having poor dispersibility into the layer of the compound (C-2). The reason is believed that the compound having methyl substituted at the 4-position such as the compound (C-2) is deprotected in the vicinity of the metal oxide that is also a Lewis acid and purpurin having high crystallinity is produced, and as a result, the surface of the metal oxide is not modified with the compound (C-2) and the grain boundary is generated.

Moreover, it becomes apparent that even in the case in which the compound (C-1) and the compound (C-3) are used as in Comparative Examples 5 and 7, the dark current is generated, and thus a low S/N ratio is exhibited. The reason is believed to be that the compound (C-1) and the compound (C-3) are compounds having a low ability of forming coordination with a metal oxide, and thus the grain boundary is generated during modification of the metal oxide surface, which does not allow a stable carrier path to be formed.

Example 9

The electrophotographic photoreceptor of Example 9 was prepared in the following manner.
—Formation of Undercoat Layer—
The undercoat layer coating liquid having the following composition was coated on a support (outer diameter 30 mm) made of aluminum (Al) by an immersion method to obtain a thickness of 3.5 μm after drying, thereby forming an undercoat layer.
[Composition of Undercoat Layer Coating Liquid]
Alkyd resin (BEKKOLITE M6401-50-S; trade name, manufactured by DIC Corporation.) . . . 33.6 parts by mass
Melamine resin (SUPER BEKKAMIN G-821-60; trade name, manufactured by DIC Corporation) . . . 18.7 parts by mass
Titanium oxide fine particles (CR-EL; trade name, manufactured by Ishihara Sangyo Kaisha Ltd., average particle diameter 0.25 μm, Rutile type) . . . 112 parts by mass
Cerium oxide fine particles (NanoTek CeO$_2$; trade name, manufactured by C.I. Kasei Co., Ltd., average particle diameter 0.01 μm) . . . 56 parts by mass
Compound (B-1) . . . 1.7 parts by mass
Methyl ethyl ketone . . . 170 parts by mass.
—Formation of Charge-Generating Layer—
Next, a charge-generating layer coating liquid including an oxotitanium phthalocyanine pigment with the following composition was coated on the above-described undercoat layer by immersion, and dried by heating, to form a charge-generating layer having a thickness of 0.2 μm.
[Composition of Charge-Generating Layer Coating Liquid]
Oxotitanium phthalocyanine pigment . . . 5 parts by mass
Butyral resin (S-LEC BMS; trade name, manufactured by Sekisui Chemical Co., Ltd.) . . . 2 parts by mass
Tetrahydrofuran . . . 80 parts by mass
—Formation of Charge-Transporting Layer—
Next, the charge-transporting layer coating liquid with the following composition was coated on the above-described charge-generating layer by immersion, and dried by heating, thereby forming a charge-transporting layer having a thickness of 12 μm.
[Composition of Charge-Transporting Layer Coating Liquid]
Bisphenol Z-type polycarbonate . . . 12 parts by mass
Charge-transporting material represented by the following structural formula . . . 8 parts by mass

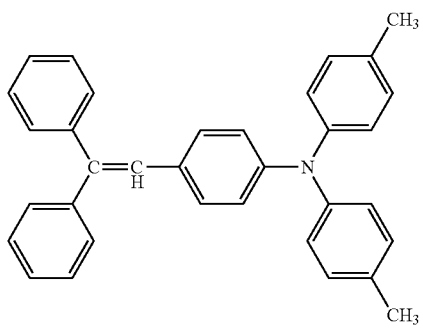 [SMILES: Cc1ccc(N(c2ccc(C)cc2)c2ccc(C=C(c3ccccc3)c3ccccc3)cc2)cc1]

Tetrahydrofuran . . . 80 parts by mass
Tetrahydrofuran solution of 1% silicon oil (KF50-100CS; trade name, manufactured by Shin-Etsu Chemical Industry Co., Ltd.) . . . 0.2 part by mass
—Formation of Crosslinked Surface Layer—
The crosslinked surface layer coating liquid having the following composition was coated on the above-described charge-transporting layer by spraying, followed by irradiation by a metal halide lamp under the conditions of an irradiation intensity of 700 mW/cm$^2$ and an irradiation time of 20 seconds, and drying at 130° C. for 30 minutes, thereby obtaining a crosslinked surface layer having a thickness of 4.0 μm. By this, the electrophotographic photoreceptor of Example 9 was prepared.
[Composition of Crosslinked Surface Layer Coating Liquid]
Radical polymerizable monomer having a polar functional group without a charge-transporting structure (acrylic acid, manufactured by Nippon Shokubai Co., Ltd.) . . . 0.05 part by mass
Radical polymerizable monomer having at least three functional groups without a charge-transporting structure (trimethylolpropane triacrylate, KAYARAD TMPTA; trade name, all manufactured by Nippon Kayaku Co., Ltd., molecular weight: 382, number of functional groups: 3, molecular weight/number of functional groups=99) . . . 9 parts by mass
Radical polymerizable compound having a charge-transporting structure represented by the following structural formula . . . 9 parts by mass

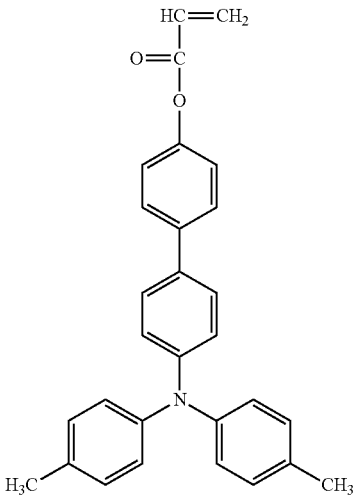

Photopolymerization initiator (1-hydroxycyclohexyl phenyl ketone, trade name: IRGACURE 184, all manufactured by Chiba Specialty Chemicals) . . . 2 parts by mass
Tetrahydrofuran . . . 100 parts by mass. λ

Example 10

An electrophotographic photoreceptor of Example 10 was prepared in substantially the same manner as that in Example 9 except that the compound (B-1) in the coating liquid for the undercoat layer in Example 9 was changed to the compound (B-2) in Example 10.

Example 11

An electrophotographic photoreceptor of Example 11 was prepared in substantially the same manner as that in Example 9 except that the compound (B-1) in the coating liquid for the undercoat layer in Example 9 was changed to the compound (B-3) in Example 11.

Example 12

An electrophotographic photoreceptor of Example 12 was prepared in substantially the same manner as that in Example 9 except that the compound (B-1) in the coating liquid for the undercoat layer in Example 9 was changed to the compound (B-5) in Example 12.

Example 13

An electrophotographic photoreceptor of Example 13 was prepared in substantially the same manner as that in Example 9 except that the compound (B-1) in the coating liquid for the undercoat layer in Example 9 was changed to the compound (B-8) in Example 13.

Comparative Example 8

An electrophotographic photoreceptor of Comparative Example 8 was prepared in substantially the same manner as that in Example 9 except that the compound (B-1) in the coating liquid for the undercoat layer in Example 9 was changed to 1-hydroxyanthraquinone in Comparative Example 8.

Comparative Example 9

An electrophotographic photoreceptor of Comparative Example 9 was prepared in substantially the same manner as that in Example 9 except that the compound (B-1) in the coating liquid for the undercoat layer in Example 9 was changed to 2-amino-3-hydroxyanthraquinone in Comparative Example 9.

Comparative Example 10

An electrophotographic photoreceptor of Comparative Example 10 was prepared in substantially the same manner as that in Example 9 except that the compound (B-1) in the coating liquid for the undercoat layer in Example 9 was changed to the compound (C-2) in Comparative Example 10.

Comparative Example 11

An electrophotographic photoreceptor of Comparative Example 11 was prepared in substantially the same manner as that in Example 9 except that the compound (B-1) in the coating liquid for the undercoat layer in Example 9 was changed to the compound (C-3) in Comparative Example 11.

[Evaluation]

The electrophotographic photoreceptor obtained in each of Examples 9 to 13 and Comparative Examples 8 to 11 was loaded in a full-collar printer "DocuCentre Color C400"; trade name, manufactured by Fuji Xerox Co., Ltd., having a contact-type electrostatic charging device and an intermediate transfer device, and the qualities (generation of abnormal densities, generation of ghosts, or generation of black spots) of printed images at the start (at the $10^{th}$ sheet) and after continuous printing of 10,000 sheets were evaluated under a high temperature and a high humidity (28° C. and 40% RH), and then evaluated in accordance with the following criteria.

The results are shown in Table 3.

—Evaluation Criteria—

<Generation of Abnormal Densities>

The generation of abnormal densities was evaluated by conducting a setting in which an image with a 20% density at the first sheet is obtained, and then visually observing the image densities of the $10^{th}$ sheet and the $10,000^{th}$ sheet, and the evaluation was performed in accordance with the following criteria.

—Evaluation Criteria—

A: The same or the like,

B: Slight reduction in density, and

C: Remarkable reduction in density.

<Generation of Ghosts>

—Evaluation Criteria—

For evaluation of ghosts, as shown in FIG. 1, the chart of patterns having the letters of G and the black region was printed, and the state in which the letters of G were shown in the black area was visually observed and evaluated in accordance with the following criteria.

Figure 1B:

A: Good or insignificant as shown in FIG. 1A,

B: Slightly noticeable as shown in FIG. 1B, and

Figure 1C:
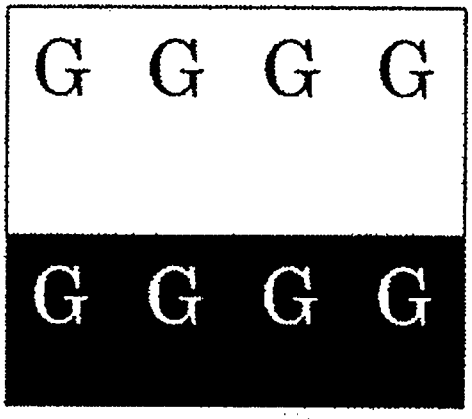

C: Clearly noticeable as shown in FIG. 1C.

<Generation of Black Spots>

For generation of black spots, white images were printed on the $10^{th}$ and $10,000^{th}$ A4-size blank white paper, and the images in the center part of the A4 size and in the 10 cm×10 cm area were visually observed and evaluated in accordance with the following criteria.

—Evaluation Criteria—

A: Good (No generation of black spots),

B: Generation of about 1 to 10 black spots having a dimension of 0.1 mm or less on the image, and C: Generation of black spots on the entire surface of the image (including the spots having a dimension of 0.1 mm or more).

TABLE 3

| | | Evaluation of images printed under a high temperature and a high humidity | | | | | |
| --- | --- | --- | --- | --- | --- | --- | --- |
| | | Images at the start | | | Images after 10,000 sheets continuous printing | | |
| | | Abnormal Densities | Ghosts | Fogging/ Black spots | Abnormal Densities | Ghosts | Fogging/ Black spots |
| Example 9 | Compound B-1 | A | A | A | A | A | A |
| Example 10 | Compound B-2 | A | A | A | A | A | A |
| Example 11 | Compound B-3 | A | A | A | A | A | A |

TABLE 3-continued

| | | Evaluation of images printed under a high temperature and a high humidity | | | | | |
|---|---|---|---|---|---|---|---|
| | | Images at the start | | | Images after 10,000 sheets continuous printing | | |
| | | Abnormal Densities | Ghosts | Fogging/ Black spots | Abnormal Densities | Ghosts | Fogging/ Black spots |
| Example 12 | Compound B-5 | A | A | A | A | A | A |
| Example 13 | Compound B-8 | A | A | A | A | A | A |
| Comparative Example 10 | 1-hydroxyanthraquinone | A | A | A | B | B | B |
| Comparative Example 11 | 2-amino-3-hydroxyanthraquinone | A | A | A | B | B | B |
| Comparative Example 12 | Compound C-2 | B | B | B | B | B | B |
| Comparative Example 13 | Compound C-3 | B | B | B | C | C | C |

As shown in Table 3, it can be seen that the electrophotographic photoreceptors of Examples 9 to 13 provide images having good image qualities while inhibiting the generation of abnormal densities, ghosts, and fogging/black spots, as compared with the electrophotographic photoreceptors of Comparative Examples 8 to 11 in which the compounds in the out of scope of the alizarin derivative compound of the present invention are used in the undercoat layer. Further, the electrophotographic photoreceptors of Examples 9 to 13 show an excellent preservation property without generation of black spots due to a leak defect.

The reason for this is thought that since the alizarin derivative compound of the present invention has high solubility in the undercoat layer coating liquid and an excellent amorphous property while having no change in the ability of forming a bond with a metal oxide fine particle, a grain boundary is not generated in the interface of the metal oxide fine particles.

According to the present invention, a preparation method for obtaining an alizarin derivative compound in a simple manner and at low cost by using purpurin as a starting material and modifying the 4-position thereof, and a novel alizarin derivative compound to which the preparation method can be applied can be provided.

According to the present invention, a surface modification method for an inorganic compound solid material using the novel alizarin derivative compound can also be provided.

In addition, according to the present invention, a photoelectric conversion film, a photoelectric conversion element, and an electrophotographic photoreceptor, having the novel alizarin derivative compound as a component can be further provided.

The foregoing description of the exemplary embodiments of the present invention has been provided for the purposes of illustration and description. It is not intended to be exhaustive or to limit the invention to the precise forms disclosed. The embodiments were chosen and described in order to best explain the principles of the invention and its practical applications, thereby enabling others skilled in the art to understand the invention for various embodiments and with the various modifications as are suited to the particular use contemplated.

All publications, patent applications, and technical standards mentioned in this specification are herein incorporated by reference to the same extent as if such individual publication, patent application, or technical standard was specifically and individually indicated to be incorporated by reference. It will be obvious to those having skill in the art that many changes may be made in the above-described details of the preferred embodiments of the present invention. It is intended that the scope of the invention be defined by the following claims and their equivalents.

The invention claimed is:

1. A method for preparing an alizarin derivative compound comprising:
   (A) preparing a compound represented by the following Formula (2) by protecting a cathecol moiety included in a compound represented by the following Formula (3) with a protecting group containing P; and
   (B) preparing an alizarin derivative compound represented by the following Formula (1) via alkylation of a 4-position of, and deprotection of the protecting group containing P at the cathecol moiety of the compound represented by Formula (2) prepared by the step (A);

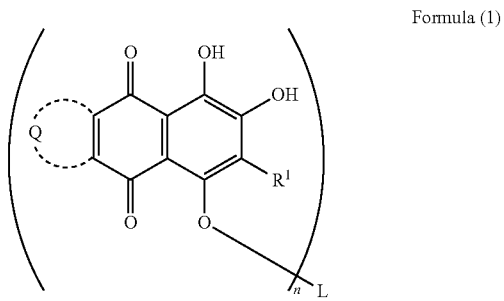

Formula (1)

wherein, in Formula (1), $R^1$ represents a hydrogen atom or a substituent; n represents an integer of 1 to 3, when n is 1, L represents —C($R^{a1}$)($R^{a2}$)($R^{a3}$); $R^{a1}$, $R^{a2}$, and $R^{a3}$ each independently represent a hydrogen atom, a substituted or unsubstituted alkyl group having 1 to 30 carbon atoms, or a substituted or unsubstituted aryl group having 6 to 30 carbon atoms; at least one of $R^{a1}$, $R^{a2}$, and $R^{a3}$ represents a substituted or unsubstituted alkyl group having 1 to 30 carbon atoms, or a substituted or unsubstituted aryl group having 6 to 30 carbon atoms; when n is 2, L represents a substituted or unsubstituted divalent linkage group having 2 to 20 carbon atoms; when n is 3, L represents a substituted or unsubstituted trivalent linkage group having 2 to 30 carbon atoms; and Q represents an atomic group which is needed to form an aromatic ring or a heteroaromatic ring with adjacent carbon atoms;

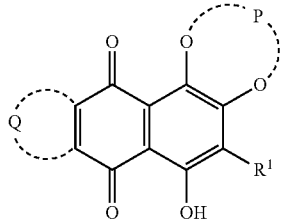

Formula (2)

wherein, in Formula (2), P represents an atomic group which includes an atom(s) selected from a hydrogen atom, a carbon atom, an oxygen atom, a sulfur atom, a silicon atom and a boron atom, and which is needed to form a ring structure with two adjacent oxygen atoms and two carbon atoms; and each of $R^1$ and Q has the same definition as $R^1$ and Q in Formula (1) respectively;

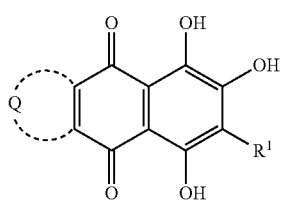

Formula (3)

and wherein, in Formula (3), each of $R^1$ and Q has the same definition as $R^1$ and Q in Formula (1) respectively.

2. The method for preparing an alizarin derivative compound according to claim 1, wherein the step (B) comprises:
(B1) preparing a compound represented by the following Formula (4) via alkylation of the 4-position of the compound represented by Formula (2); and
(B2) preparing the alizarin derivative compound represented by Formula (1) via deprotection of the protecting group containing P at the cathecol moiety of the compound represented by Formula (4) prepared by the step (B1);

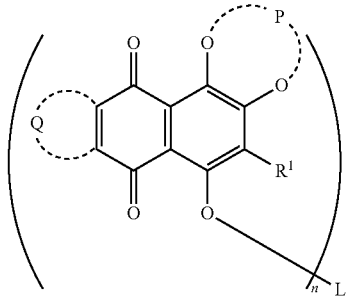

Formula (4)

wherein, in Formula (4), P has the same definition as P in Formula (2); and each of $R^1$, L, n and Q has the same definition as $R^1$, L, n and Q in Formula (1) respectively.

3. An alizarin derivative compound represented by the following Formula (5);

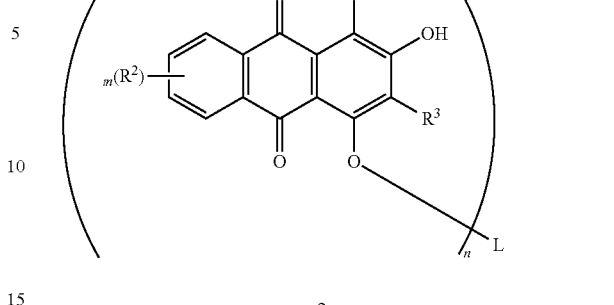

Formula (5)

wherein, in Formula (5), $R^2$ represents a hydrogen atom, a substituted or unsubstituted alkyl group having 1 to 30 carbon atoms, a substituted or unsubstituted aryl group having 6 to 30 carbon atoms, or a substituted or unsubstituted alkoxy group having 1 to 30 carbon atoms; m represents an integer of 0 to 4; $R^3$ represents a hydrogen atom, a substituted or unsubstituted alkyl group having 1 to 30 carbon atoms, a substituted or unsubstituted aryl group having 6 to 30 carbon atoms, or a substituted or unsubstituted alkoxy group having 1 to 30 carbon atoms; n represents an integer of 1 to 3; when n is 1, L represents $-C(R^{a1})(R^{a2})(R^{a3})$; $R^{a1}$, $R^{a2}$, and $R^{a3}$ each independently represent a hydrogen atom, a substituted or unsubstituted alkyl group having 1 to 30 carbon atoms, or a substituted or unsubstituted aryl group having 6 to 30 carbon atoms; at least one of $R^{a1}$, $R^{a2}$, and $R^{a3}$ represents a substituted or unsubstituted alkyl group having 1 to 30 carbon atoms, or a substituted or unsubstituted aryl group having 6 to 30 carbon atoms; when n is 2, L represents a substituted or unsubstituted divalent linkage group having 2 to 20 carbon atoms; and when n is 3, L represents a substituted or unsubstituted trivalent linkage group having 2 to 30 carbon atoms.

4. The alizarin derivative compound according to claim 3, wherein the alizarin derivative compound represented by Formula (5) is an alizarin derivative compound represented by the following Formula (6);

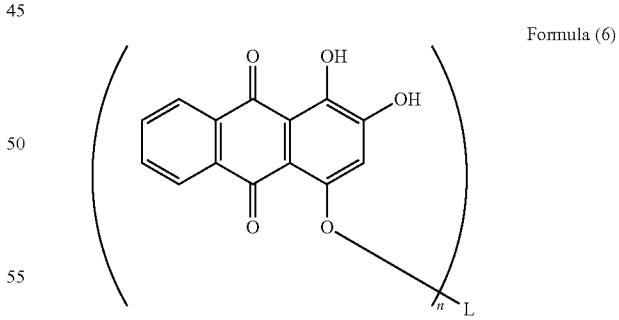

Formula (6)

wherein, in Formula (6), each of n and L has the same definition as n and L in Formula (5) respectively.

5. A surface modification method for an inorganic compound solid material, the method comprising bonding the alizarin derivative compound according to claim 3 to a surface of an inorganic compound solid material through an oxygen atom obtained by removal of a hydrogen atom from at least one hydroxyl group contained in the alizarin derivative compound.

6. The surface modification method for an inorganic compound solid material according to claim 5, wherein the inorganic compound solid material is a metal oxide.

7. The surface modification method for an inorganic compound solid material according to claim 5, wherein the inorganic compound solid material is a fine particle of a metal oxide.

8. The surface modification method for an inorganic compound solid material according to claim 6, wherein the metal oxide is selected from the group consisting of $TiO_2$, $Al_2O_3$, $SiO_2$, $ZrO_2$ and ZnO.

9. A photoelectric conversion film comprising the alizarin derivative compound according to claim 3.

10. A photoelectric conversion element comprising the alizarin derivative compound according to claim 3.

11. An electrophotographic photoreceptor comprising a conductive base, an undercoat layer on the conductive base and a photoconductive layer, wherein the undercoat layer comprises the alizarin derivative compound according to claim 3.

* * * * *